(12) United States Patent
Bour et al.

(10) Patent No.: US 6,452,670 B1
(45) Date of Patent: Sep. 17, 2002

(54) PROCESS AND INSTRUMENT FOR CHECKING THE BONDING OF THE CELLULAR CORE OF A HONEYCOMB TO A SKIN

(75) Inventors: Jean-Luc Bour, Dammarie les Lys; Gérard Weiss, Mennecy, both of (FR)

(73) Assignee: Societe Nationale d'Etude et de Construction de Moteurs d'Aviation "Snecma", Paris (FR)

( * ) Notice: Subject to any disclaimer, the term of this patent is extended or adjusted under 35 U.S.C. 154(b) by 0 days.

(21) Appl. No.: 09/429,306

(22) Filed: Oct. 28, 1999

(30) Foreign Application Priority Data

Oct. 29, 1998 (FR) .............................................. 98 13564

(51) Int. Cl.$^7$ .............................................. G01N 21/88
(52) U.S. Cl. .................... 356/237.1; 356/237.1
(58) Field of Search ........................ 356/237.1, 241.1

(56) References Cited

U.S. PATENT DOCUMENTS 5,548,400 A * 8/1996 Bourguinat .............. 356/241.1

FOREIGN PATENT DOCUMENTS

| EP | 0 624 788 A1 | 11/1994 |
| FR | 668 493 A | 11/1929 |
| FR | 2 716 260 A1 | 8/1995 |

* cited by examiner

Primary Examiner—Richard A. Rosenberger
(74) Attorney, Agent, or Firm—Oblon, Spivak, McClelland, Maier & Neustadt, P.C.

(57) ABSTRACT

The invention provides a process for checking the bonding of the cellular core of a honeycomb to a skin, said process comprising the steps of: using a light source to illuminate a so-called illuminated zone on the free surface of the honeycomb so as to illuminate the interior of the cells opening out into said illuminated zone, and detecting the emergent light exiting the cells in a so-called observed zone. The minimum distance between said illuminated zone and said observed zone is denoted E and defines a direction D, the distance E being at least equal to the width L1 of the cell mouths measured in the direction D, so as to make it impossible for the illuminated zone and the observed zone to be simultaneously above the mouth of one and the same cell. The invention also provides an instrument for implementing the process.

31 Claims, 7 Drawing Sheets

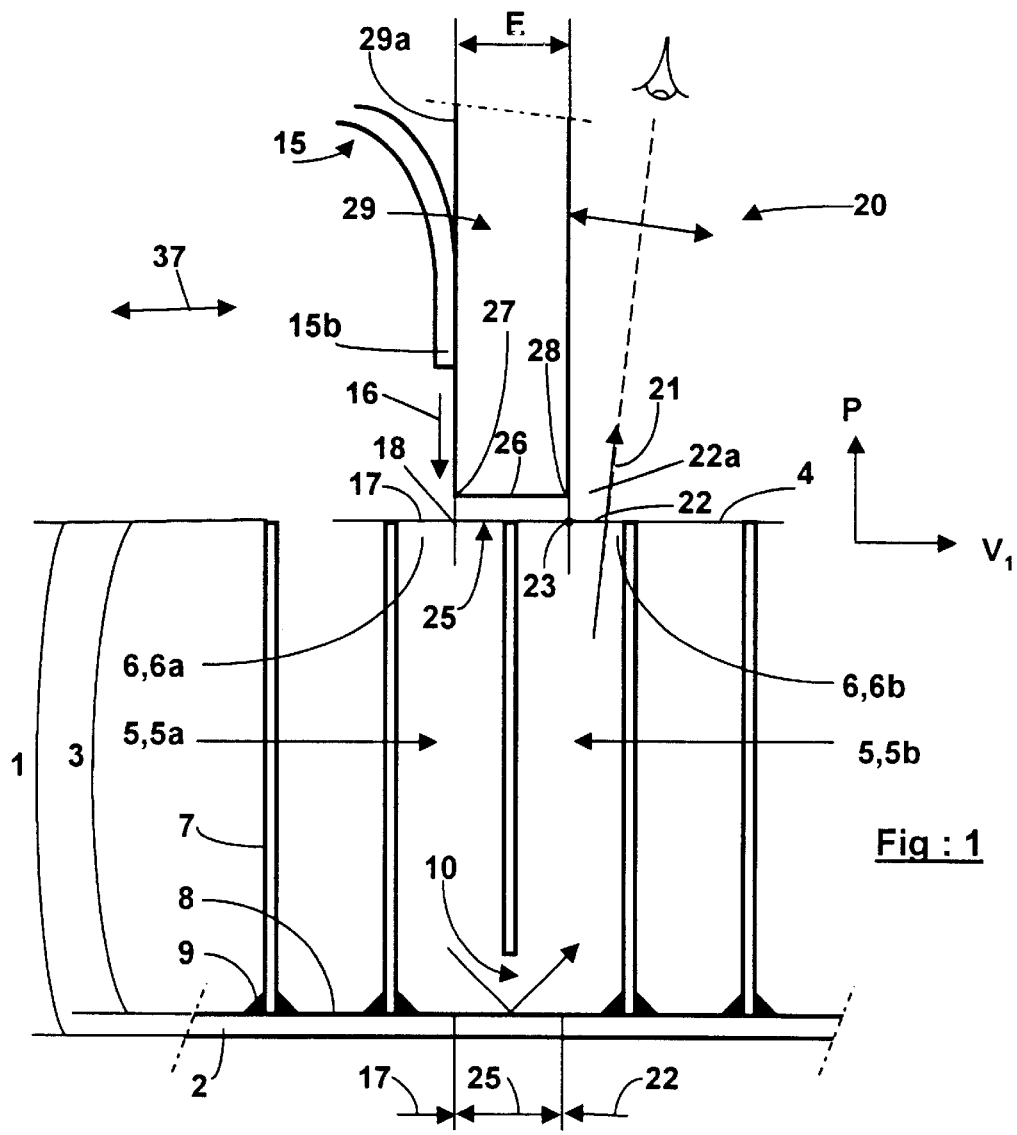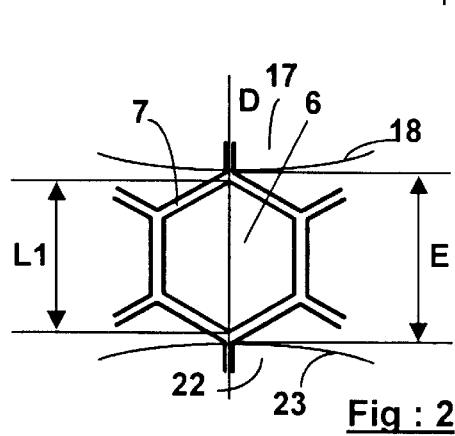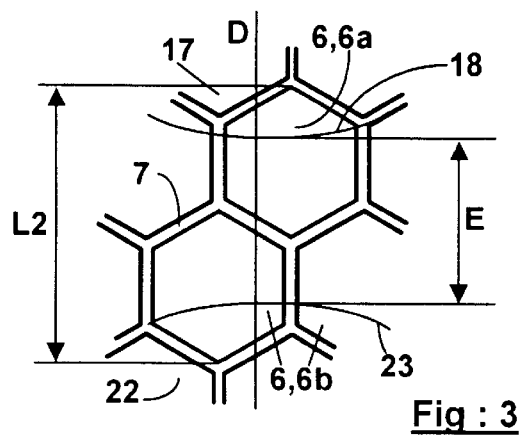
Fig : 1
Fig : 2
Fig : 3

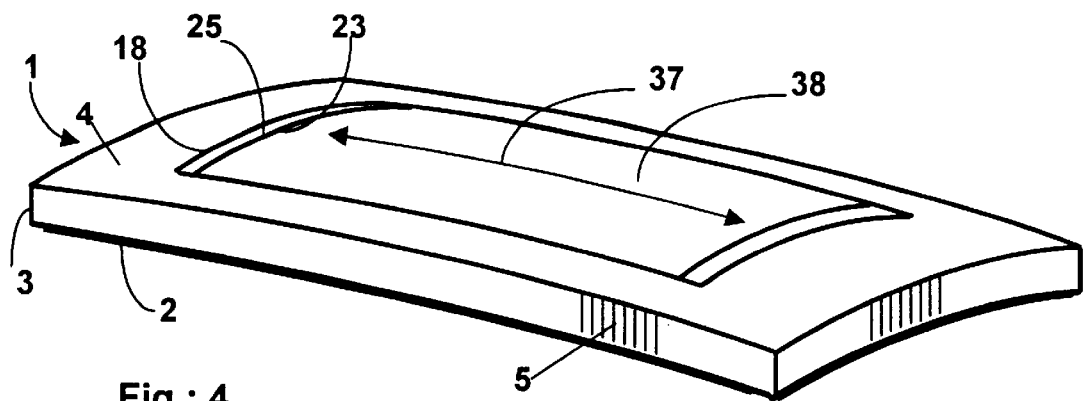
Fig : 4
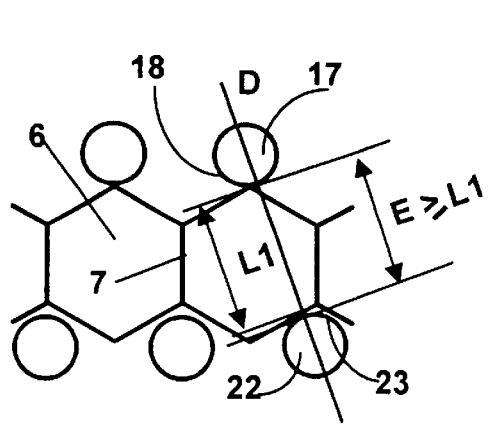
Fig : 5
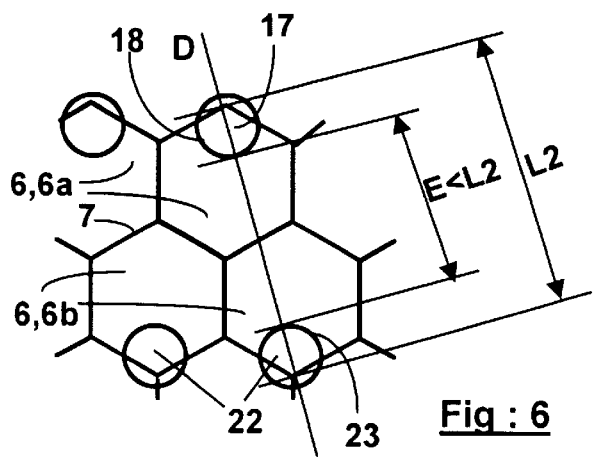
Fig : 6
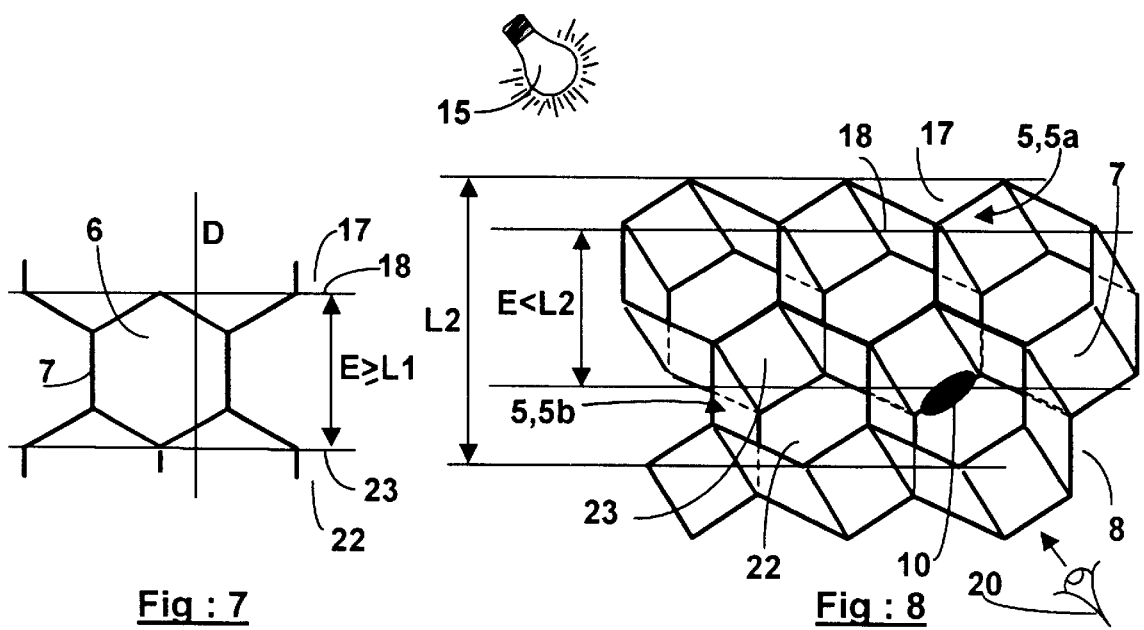
Fig : 7
Fig : 8

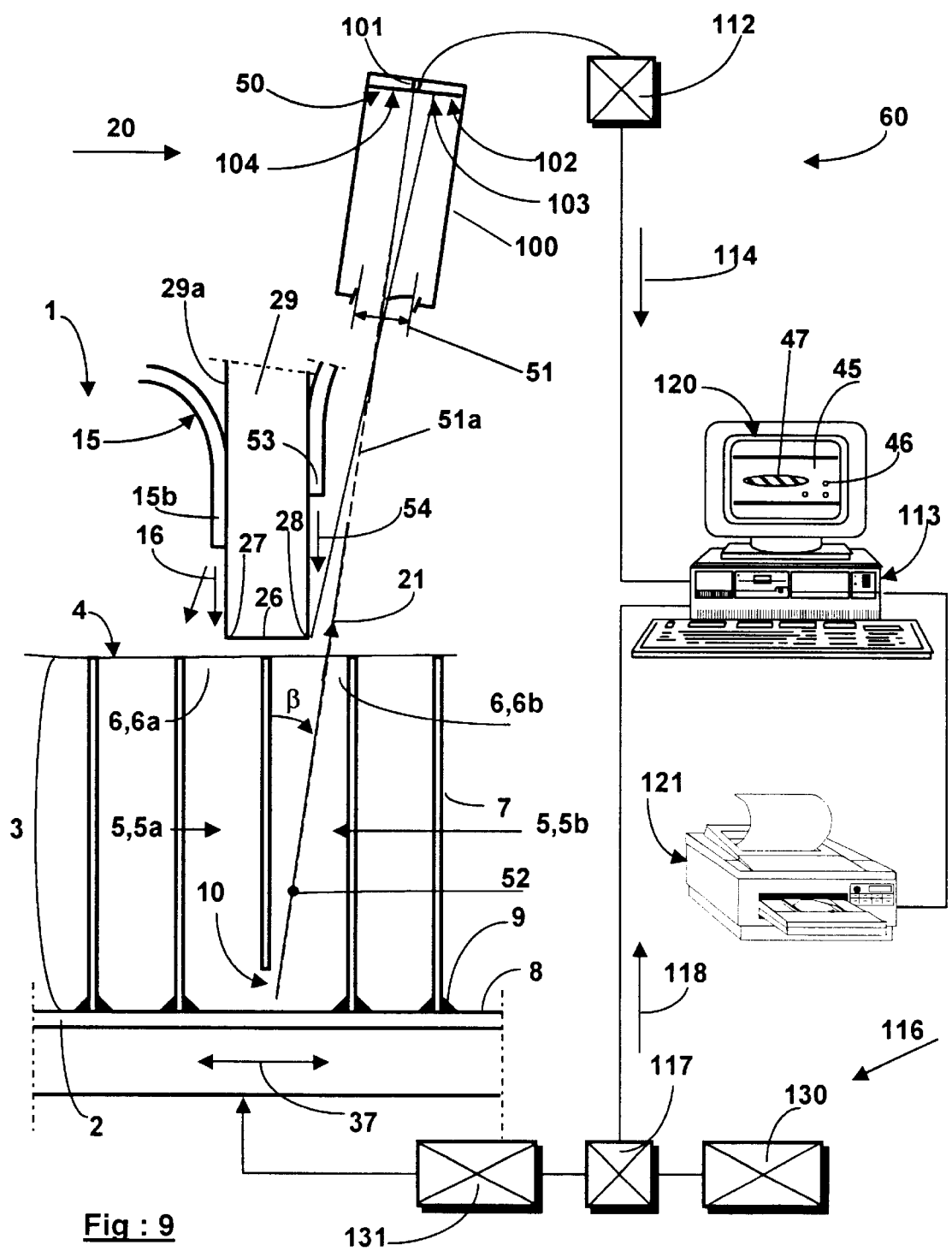
Fig : 9

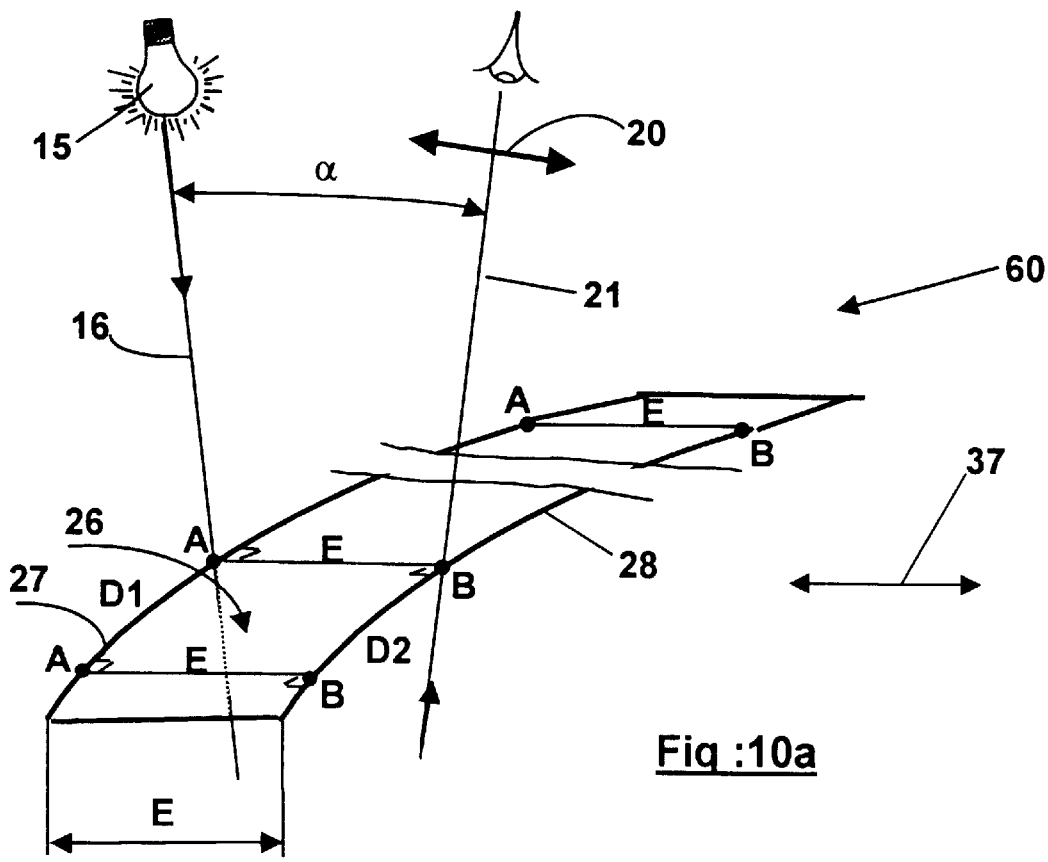
Fig :10a
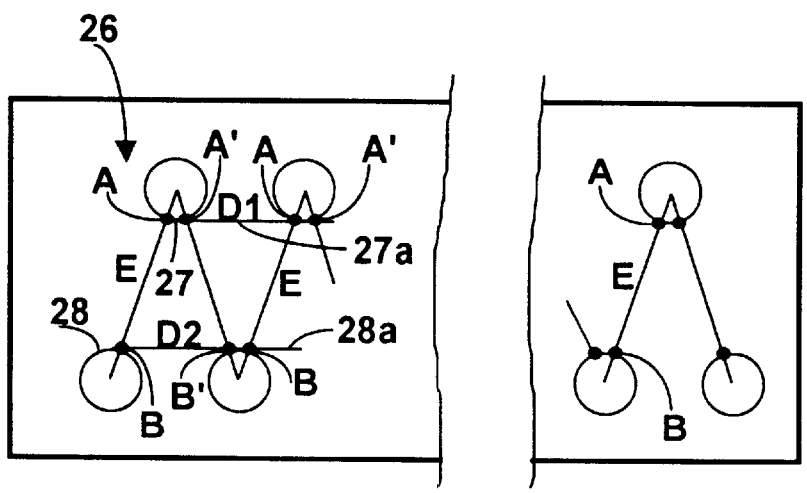
Fig : 10b

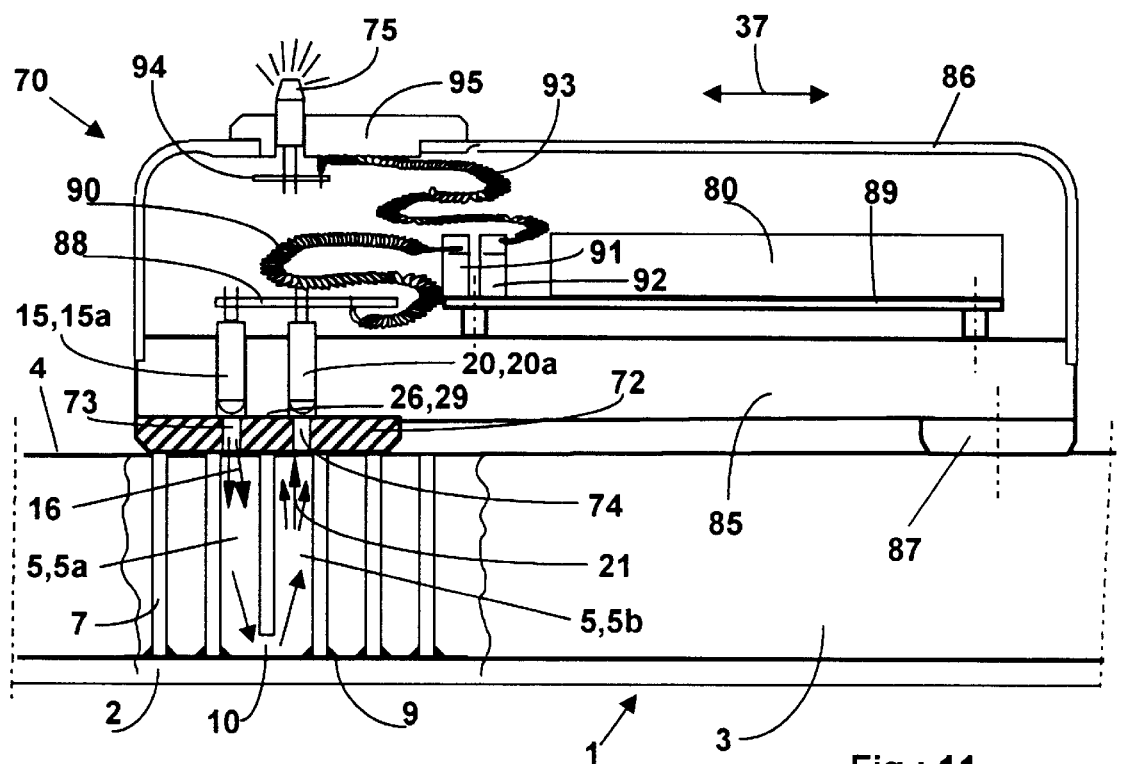
Fig : 11
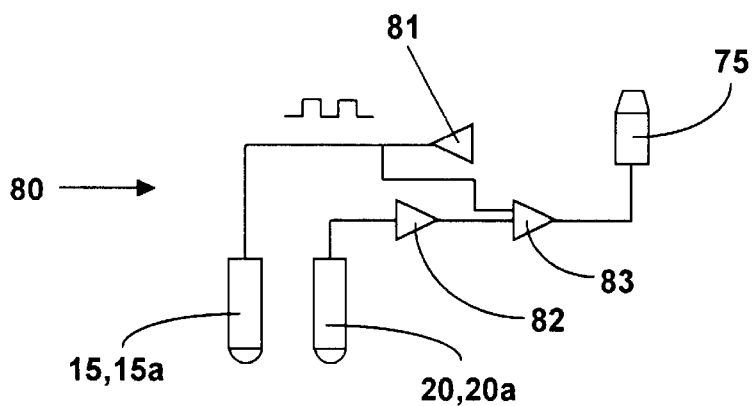
Fig : 12

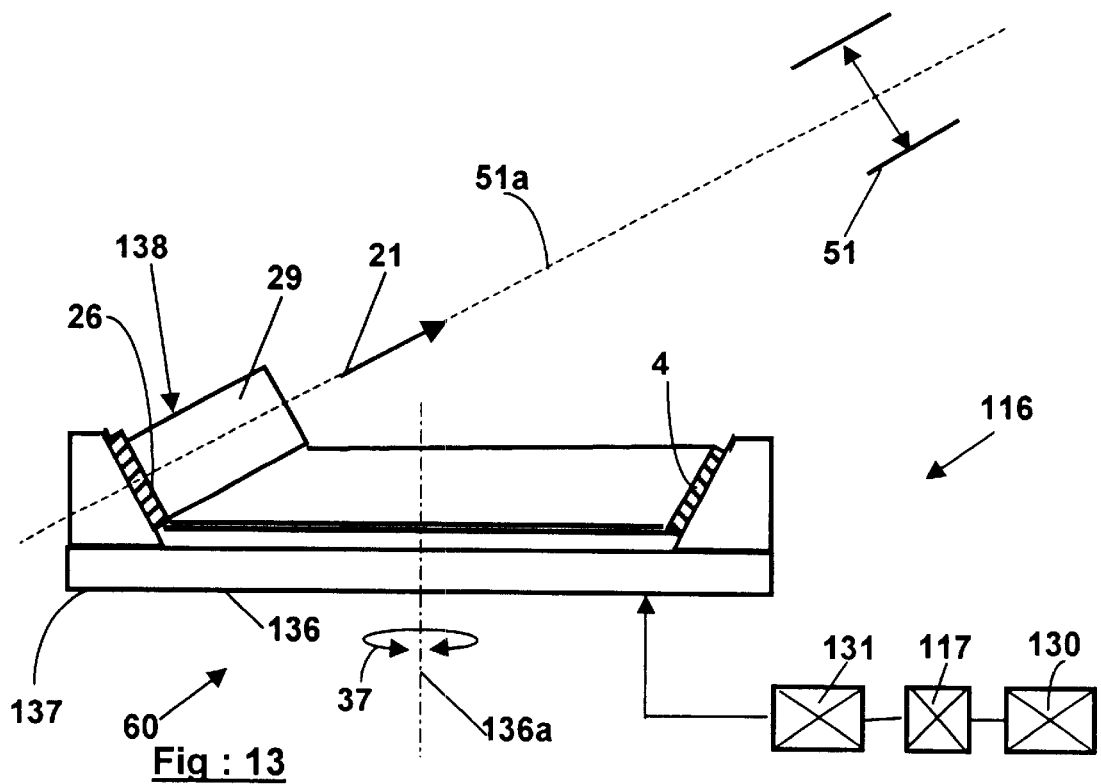
Fig : 13
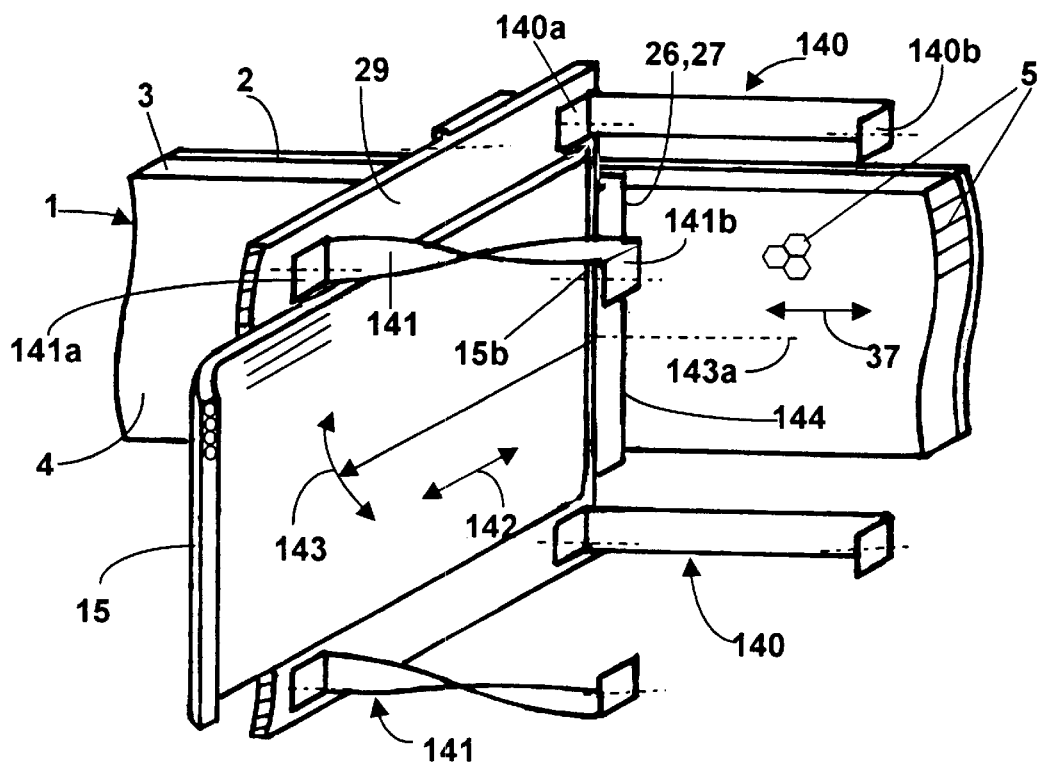
Fig : 14

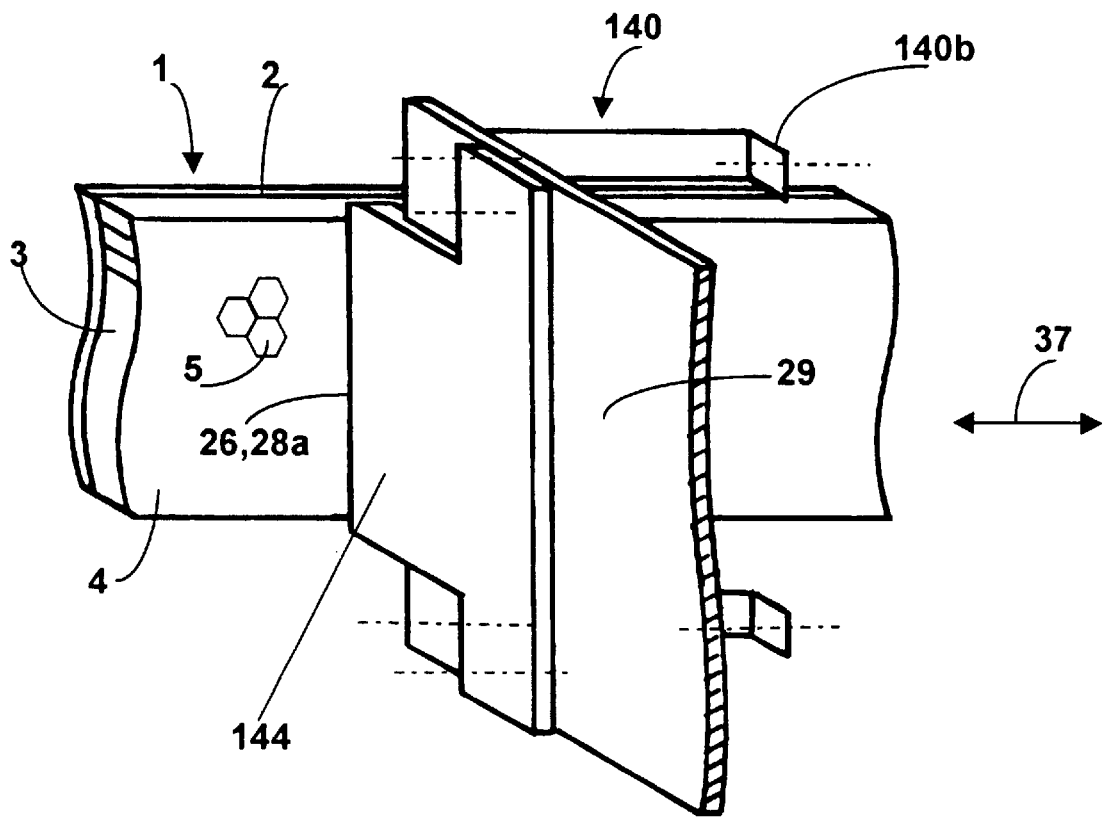
Fig : 15

PROCESS AND INSTRUMENT FOR CHECKING THE BONDING OF THE CELLULAR CORE OF A HONEYCOMB TO A SKIN

BACKGROUND OF THE INVENTION

1. Field of the Invention

The invention relates to laminated honeycomb structures, and more especially to the checking of the bonding of the cellular core of the honeycomb to a skin. In this regard the invention proposes a checking process and a specially designed device for implementing the present process.

2. Summary of the Prior Art

In what follows, a laminated honeycomb structure will simply be referred to as a "honeycomb". Honeycombs are well known in industry, and especially in aeronautics for making in particular turbomachine seal packings, acoustic panels or for constructing thin and rigid panels such as nozzle flaps or aircraft structures. Honeycombs usually take the form of flat or shaped plates, the form of frustoconical monobloc ferrules or the form of sectors of these same ferrules. The term monobloc should be understood to mean one-piece. At this stage of manufacture the honeycomb comprises a cellular core bonded via one of its sides to a skin. The skin is a flat or bowed plate which can be of the same material as the cellular core or of a different material. The cellular core takes the form of adjacent cells separated by partitions extending in the direction of the thickness of the honeycomb, the ends of the partitions on one side of the cellular core being bonded to the skin, the cells opening out on the other side, these cells customarily being hexagonal, but sometimes rectangular, these partitions customarily being substantially perpendicular to the surface of the honeycomb, and more rarely inclined.

The making of the honeycomb comprises a tricky operation, i.e. the bonding of the cellular core to the skin, this bonding being done for example by gluing or brazing. The defects in bonding the partitions to the skin appear in an isolated manner or over an expanse grouping together several mutually adjacent cells. These defects can be an absence or a localized insufficiency of binding agent or an incipient melting of the partitions of the cells when using a binder such as a high-resistance brazing whose melting point is near that of the metallic alloy constituting the honeycomb. Such defects are manifested by the appearance on the bottom of the cells of spaces between the partitions of the cells and the skin, these spaces placing the cells in communication with one another.

In the case of hexagonal cells, the cellular core can be made from strips whose width is equal to the thickness of the cellular core, said strips each being folded to form a succession of half-hexagons, each fold constituting one of the six partitions of each hexagonal cell, said strips thereafter being disposed side by side and assembled together, each cell thereby comprising two double opposite partitions. In the case of braised honeycombs, part of the brazing used to bond the cellular core to the skin rises up by capillarity between the two partitions constituting a double partition, and effects the bonding thereof. In any event and regardless of the mode of bonding used, this bonding together of the double partitions must also be checked.

The checking of the brazing runs up against three sorts of difficulties industrially, i.e.:

a honeycomb must be able to be checked rapidly, despite the high number of its cells, the defects are situated essentially on the bottom of the cells whilst the depth of said cells often exceeds ten times their mean diameter, the cells may be of small sizes, with a width of less than a millimeter, it must be possible to detect point defects involving only two adjacent cells, and not merely expanses of defects extending over several cells, or even a large number of cells.

In turbomachines, especially turboengines for aircraft, the honeycombs are mainly used as abradable seal packings between the rotating parts and the fixed parts. Cells are customarily hexagonal with a major diameter of less than 3 mm, typically 1.8 mm. Diameters dropping to 0.6 mm are envisaged. For example, a 45×145 mm frustoconical sector comprises around 3000 cells of 1/16th of an inch, i.e. around 1.6 mm, and a monobloc ferrule of width 45 mm and diameter 800 mm comprises around 53,000 thereof. In aircraft structures and pods, the diameter of the cells may reach 36 mm, this again representing a density of around 1200 cells per square meter.

The surface of the cellular core of the honeycomb which is opposite the skin will be referred to as the "free surface". To simplify the language and unless specified to the contrary, the expressions "on the free surface", "above" etc. will be used to specify that which is outside the honeycomb on the free surface side, and the expressions "under the free surface", "below" etc. will be used to specify that which is depthwise in the honeycomb, without prejudging the actual orientation of said free surface in space.

A widespread so-called "capillarity-based" checking process consists in filling the cells of the honeycomb with a solvent such as fluorinated trichloroethane by dipping in a vessel, in inclining the honeycomb and in visually examining its surface under black light. When cells are placed in communication via defects of bonding, liquid flows from one cell to another, and the openings of the cells concerned show up with a different intensity. This process is rapid, but nevertheless has three drawbacks:

it emits polluting vapors, especially with regard to the operator, it demands large vessels when the panels to be checked are of large size, it demands an additional operation of removing the liquid from the cells, this becoming problematic when the cells are of small size or else when the honeycomb is an annulus and the openings of the cells are pointing inward.

A process is also known which consists in heating the honeycomb through the side of the skin and in examining the emission of infrared from the other side, this emission being weaker in the expanses exhibiting brazing defects, since the thermal conductivity in the thickness direction of the honeycomb is lower there. This process is however reserved for honeycombs of large size, since the edge effects are important. Moreover, this edge effect masks point defects. Consequently, this process only allows detection of expanses of defects extending over numerous cells.

The patent FR-2,716,260 also granted in the United States under number U.S. Pat. No. 5,548,400 discloses a checking process consisting in strongly illuminating a cell by bringing in front of its opening an optical fiber connected to a light source, and in detecting the weak light passing through a bonding defect into the adjacent cells by bringing above said adjacent cells optical fibers connected to optoelectronic detection means, the optical fibers being held by a solid support laid on the surface of the honeycomb, this support being positioned with respect to the openings of the cells by pegs penetrating into neighboring cells. This process nevertheless has the drawback of being very low, since the instrument must be positioned in succession in front of each cell to be examined, and the use of a machine of the robot arm type would merely reduce this drawback without eliminating it. Moreover, the inaccuracy in the geometry of the cells precludes the assembling of a sizable number of instruments for checking several cells simultaneously.

Hand-held scanners which can be connected to microcomputers and make it possible to digitize a document with the aid of specialized software are also known. Such scanners comprise a light source illuminating a line on the document, an objective constructing a real image of the illuminated line, an array of photoelectric receptors disposed on the real image of the illuminated line, a sampling analog/digital converter producing a digital signal consisting of a series of doublets indicating the intensity of the signal received by each photoelectric receptor as well as the position of the receptor in the array, and means for measuring the displacement of the scanner on the surface of the document and for producing a digital signal indicating the displacement. These two digital signals are transmitted to a microcomputer equipped with specific software, said software making it possible to reconstruct the image of the document, to store this image in the chosen standard, for example in the "bitmap" or BMP format, and to display said image of the document on the screen of the microcomputer. The measurement of the displacement can be performed by a wheel in contact with the document, said wheel comprising toward its periphery a plurality of regularly spaced holes marching past a photoelectric receptor, said photoelectric receptor producing electrical pulses which are subsequently totalized by a counter so as to deduce the displacement thereof. The holes can be replaced by magnetized zones, and the photoelectric receptor by a magnetic reading head. In another embodiment, the displacement of the scanner is motorized, and the aforesaid wheel is disposed on a mechanical transmission connected to the motor. Even by modifying the adjustment of the objective, such scanners do not make it possible to show up the defects on the bottom of the cells of the honeycomb.

SUMMARY OF THE INVENTION

A first object of the invention is to provide a rapid and nonpolluting process for checking the bonding of the cellular core of a honeycomb to a skin.

A second object of the invention is to provide a rapid process for establishing a map of the bonding defects.

Subsidiarily, a third object of the invention is to provide a checking process which is tolerant to the geometrical irregularities of the honeycomb.

A fourth object of the invention is to provide a specially designed instrument for implementing the process for checking bonding defects.

A fifth object of the invention is to provide a specially designed instrument for implementing the process for mapping bonding defects.

According to the invention, the first object is achieved by a process for checking the bonding of the cellular core of a honeycomb to a skin, said honeycomb comprising a cellular core consisting of adjacent cells delimited laterally by partitions, said core being bonded at one side to a skin whilst at this stage of manufacture the other side constitutes a free surface here the mouths of said cells are open, said process comprising the following steps:

using a light source to illuminate a so-called illuminated zone on the free surface of the honeycomb, so as to illuminate the interior of the cells opening out into said illuminated zone; and detecting the so-called "emergent" light exiting the cells in a so-called observed zone likewise on the free surface of the honeycomb, the minimum distance between said illuminated zone and said observed zone being denoted E and defining a direction D, the distance E being at least equal to the width L1 of the mouths of the cells measured in the direction D.

The minimum distance E is taken between a geometrical point A at the edge of the illuminated zone and a geometrical point B at the edge of the observed zone, the direction D being parallel to the geometrical segment AB.

It will be understood that such an arrangement prevents the illuminated zone and the observed zone from being present simultaneously above the mouth of the same cell, this being so regardless of the relative position of said illuminated zone and of said observed zone with respect to the cells. Therefore, it is not necessary to position the illuminated zone and the observed zone above the checked partitions, it is sufficient "to pass above". Specifically, as a cell cannot be located simultaneously under the illuminated zone and the observed zone, the light emerging into the observed zone can originate only from the incident light which has passed through a defect, and not from the incident light exiting directly from the illuminated cell. Thus, when the illuminated zone and the observed zone are in a favorable position, that is to say on either side of partitions containing defects, an emergent light appears in the observed zone and can be detected by the process. In other cases, an emergent light of this kind cannot appear. Since a check can be performed at a location of the free surface of the honeycomb simply "by passing above", checks can rapidly be performed at different locations of said free surface.

The terms illumination limit and observation limit will respectively designate the limits overlooking one another of the illuminated zone and of the observed zone. The geometrical points A and B are obviously on said illumination limit and said observation limit respectively. Additionally, the illuminated zone and the observed zone need not be very extensive. A width of at most equal to E is sufficient in practice, the width of the illumination zone being taken from the illumination limit, and the width of the observation zone being taken from the observation limit.

The process forming the subject of the present invention should not be confused with the process disclosed by the aforesaid patent FR-2,716,260. Thus, in this patent the light source and the light receptor are a distance apart which is smaller than the width of the cells, so that each can be placed right opposite two adjacent cells. If said light emitter and said light receptor are not correctly positioned on the free surface of the honeycomb, they may then be simultaneously located above the same cell, the incident light illuminating a cell then being able to exit from this same cell through the observed zone and therefore to produce a false flaw signal. Accurate means of positioning, such as pegs, are therefore indispensable, thereby considerably slowing down the checking process.

Advantageously, the width E is less than the width L2 of the openings of two mated adjacent cells, said width L2 being likewise taken in the direction D. Such an arrangement makes possible the simultaneous presence of the illuminated zone above the opening of a first cell and of the observed zone above the opening of a second cell adjacent to the first, thus making it possible to detect a defect limited to the partition between these two adjacent cells. The term "openings of two mated adjacent cells" should be understood to mean the assembly constituted by the two openings in the mutually relative positions which they occupy in the honeycomb. In practice, the person skilled in the art will tend to reduce the value E to as near to L1 as possible. Therefore, during the detection of a defect, a more sizable part of the illuminated cell is covered by the illuminated zone, thus making it possible to inject more light into said illuminated cell and thereby to increase the intensity of the observed light. Likewise, a more sizable part of the observed cell is covered by the observed zone, thus facilitating the detection of any emergent light. In practice, the person skilled in the art will however adopt a difference E−L1 which is sufficient to take into account the dimensional tolerances of the cells.

It will be noted that the tolerance of the process to the variations in the direction D is good in the case of hexagonal cells whose shape approximates to a circle. In the case where the width E is at least equal to a major diameter of the cells, the direction D may be any.

Advantageously, the intermediate zone, between the illumination and observation limits on the free surface of the honeycomb, will be covered by a mask which is opaque to light, said mask being delimited laterally by a so-called "illumination" edge and a so-called "observation" edge opposing one another, said illumination edge having the same shape as the illumination limit and being positioned above it, said observation edge likewise having the same shape as said observation limit and being positioned above it, said illumination edge being touched by the incident light preferably over its entire length.

Such a mask makes it possible to obstruct the stray light exiting from an illuminated cell in the intermediate zone, and thereby to permit the detection of defects of small size which therefore produce only a weak emergent light. Specifically, this emergent light being naturally weak by comparison with the incident light from which it originates, the stray light exiting directly from the illuminated cells under the intermediate zone would dazzle the means of detection of the emergent light, said means of detection then no longer being able to discern only the emergent light originating from consequent defects. By obstructing this stray light, the mask therefore enables weak emergent lights originating from smaller defects to be rendered discernible.

It will be understood that the mask cooperates with the illumination edge and the observation edge so that illumination and observation limits are rendered sharper, this making it possible to check smaller-sized cells. Specifically, the shadow cast by the mask and by the illumination edge on the free surface of the honeycomb creates the intermediate zone, the illumination limit being the projection onto said free surface of the illumination edge illuminated by the incident light. Likewise, the observation edge sharply delimits the observed zone and therefore creates the observation limit. It is also understood that the blurring of the illumination limit and of the observation limit must be weak comparatively with the width L1 of the cells. Thus, sharper illumination and observation limits therefore make it possible to check cells of smaller width.

The person skilled in the art will position the illumination edge and the observation edge against the free surface of the honeycomb or in a close neighborhood thereof. It is understood that the allowable distance between the mask and the free surface of the honeycomb is dependent on the properties of the light source and the means of detection of the emergent light. Thus, in the case where the light source and the means of detection are hardly directional, the mask will have to be practically in contact with the free surface of the honeycomb. Conversely, in the case where the light source and the detection means are directional, it becomes possible to distance the mask from the free surface and to thus improve the tolerance of the process to irregularities of said free surface. In practice, a distancing at most equal to 2×E will be adopted, i.e. of between zero and twice the width E of the mask, so that the mask retains sufficient effectiveness.

In what follows and so as to simplify the language, the term "in front of the mask" will denote that which is on the same side of the mask as the honeycomb, and "behind the mask" that which is on the other side.

Advantageously, the incident light supplied by the light source is substantially perpendicular to the free surface of the honeycomb. Such an arrangement enables the position of the illumination limit on the free surface of the honeycomb to be kept substantially constant with respect to the mask, this despite any variations in the distance between the mask and the free surface, said variations originating from irregularities of said free surface. Thus, the tolerance of the process to geometrical irregularities of the free surface is improved, as is the capacity of the process to check smaller-width cells.

Advantageously, the illumination limit and the observation limit extend over N consecutive cells, N being at least equal to three. Such an arrangement extends the check to N consecutive cells between said illumination limit and said observation limit, said check of the N cells remaining simultaneous, and therefore makes it possible to accelerate the checking of a honeycomb. In practice, the person skilled in the art would use values of N at least equal to 15 or even 50 or more, so as to simultaneously check a larger number of cells, N being limited only by the irregularities of the free surface of the honeycomb and by the capacity of the means used to tolerate said irregularities.

Advantageously, the illumination limit and the observation limit are moved together along a geometrical line of displacement at the free surface of the honeycomb. Such an arrangement makes it possible to check by scanning the cells situated along the geometrical line of displacement, and thereby to accelerate the check. The term "moved together" should be understood to mean that they retain their relative positions with respect to one another during the movement. It is in fact understood that there is no longer any need to position the illumination limit and the observation limit on either side of each of the partitions of the cells along the geometrical line of displacement. The check can be performed according to a continuous scan, the process making it possible to detect any defect when the illumination limit and the observation limit arrive in a favorable position, that is to say on either side of a partition, the process detecting nothing but not producing any false signals in the converse case either.

In a preferred embodiment of the invention, the illumination limit and the observation limit extend over N consecutive cells, N being at least equal to three, said illumination limit and said observation limit being moved together along a geometrical line of displacement at the free surface of the honeycomb. Such an arrangement makes it possible to check in a single scan the geometrical surface generated by the joint displacement of the illumination limit and of the observation limit along this geometrical line of displacement, and hence to accelerate the checking of the brazing of the honeycomb. It will be understood that the speed of the check is proportional to the product N×$V_0$, $V_0$ being the speed of displacement along the geometrical line of displacement.

In a first embodiment of the invention, the space above the observed zone is cleared, and the detection of the emergent light is visual. This process has the advantage of simplicity but it must be reserved for occasional checks owing to the fatigue which it would otherwise impose on the operator. The operator can also observe the emergent light through an optical magnifying glass, especially in the case where the cells are small. In the case where the intermediate zone extends over a sizable number of cells, the magnifying glass can be cylindrical.

According to the invention, the second object is achieved by a process for checking the bonding of the cellular core of a honeycomb to a skin, the illumination and observation limits extending over N consecutive cells, N being at least equal to three, said illumination and observation limits being moved together along a geometrical line of displacement at the free surface of the honeycomb, the process being noteworthy in that:

the joint displacement of the illumination limit and of the observation limit along the geometrical line of displacement is measured, the positions of the emergent light appearing along the observation limit are marked, the appearances of the emergent light are indicated on a system of coordinates X,Y, the measurement of the displacement being plotted on one of the coordinates X,Y and the corresponding positions of the emergent light being plotted on the other coordinate Y,X.

It will be understood that the process thus makes it possible to generate point by point the map of honeycomb bonding defects.

According to the invention, the third object is achieved by a process for checking the bonding of the cellular core of a honeycomb to a skin, the process being noteworthy in that the observed zone is continuous, in that a real optical image of the observed zone is constructed with the aid of an objective, and in that the emergent light is detected on the basis of said real optical image. Such an arrangement makes it possible to separate the emergent light from any stray lights, and thereby substantially to increase the tolerance of the system to irregularities of the free surface of the honeycomb and to said stray lights. It will in fact be understood that the real optical image shows up the emergent light passing through the brazing defects in the form of small light spots which are sharper or less sharp according to the adjustment of the objective, the brightness of said spots being considerable because the objective naturally concentrates the emergent light. On the real image, these light spots are then more easily distinguished:

from the stray lights illuminating the observed surface, for example by passing between the free surface of the honeycomb and the mask, these stray lights reproducing the design of the cells more or less sharply on the real image, from the stray lights generally arriving at the objective and dispersing as a low-intensity general fog on the real image with respect to the light spots representing the defects.

Combined with an incident light perpendicular to the free surface of the honeycomb, the process makes it possible to tolerate without difficulty a discrepancy, between the free surface of the honeycomb and the mask, of as much as twice the width E of the mask. The permanent physical contact between the mask and the free surface of the honeycomb is therefore not necessary.

In a particular form of implementation of the process, the objective is accommodated on the bottom of the cells, so as to give a sharp image of the defects.

According to the invention, the fourth object is achieved by an instrument for checking the bonding of the cellular core of a honeycomb to a skin by the process of the invention, said instrument comprising:

a) an opaque mask delimited laterally by an illumination edge and an observation edge opposite said illumination edge, b) a light source disposed at the rear of the mask, said light source being secured to the mask, said light source producing an incident light beam going from the rear of the mask to the front of the mask, said beam being partially cut by the mask and the illumination edge, said mask thus extending partially outside the beam on the observation edge side, said observation edge itself being outside said beam, c) means for detecting any emergent light going from the front to the rear of the mask, and therefore in the opposite direction to the incident light, said detection means being disposed behind the mask, and therefore on the same side as the light source said detection means being secured to the mask, said emergent light passing in front of the observation edge in the neighborhood thereof, wherein at M successive geometrical points A on the illumination edge and at M successive geometrical points B on the observation edge, M being at least equal to five, the distance AB between the illumination edge and the observation edge is a minimum and equal to E, the distance D1 between two geometrical points A being at least equal to 0.5×E, the distance D2 between two geometrical points B also being at least equal to 0.5×E, the M geometrical points A forming an open line whose two geometrical points A situated at its ends are a distance apart greater than that of any other doublet of geometrical points A, the M geometrical points B likewise forming an open line whose two geometrical points B at its ends are a distance apart greater than that of any other doublet of geometrical points B.

It will be understood that the position of the light source and of the means of detection of any emergent light define the so-called "rear" side of the mask, said light source and said means of detection both being at the rear of the mask, the honeycomb to be checked being disposed "in front of" the mask, said light source possibly however protruding laterally from the mask on the illumination edge side, said means of detection likewise possibly protruding laterally from the mask on the observation edge side.

It will be understood that the mask can be disposed flat on a larger surface than itself or in the neighborhood of this surface, said surface possibly being the free surface of a honeycomb. The light source makes it possible to illuminate this surface from the rear of the mask over a so-called illuminated zone, said illuminated zone being delimited by a sharp edge or "illumination limit" produced by the shadow cast by the mask and by the illumination edge on the surface. The means of detection of any emergent light make it possible to observe from the rear of the mask a so-called observation zone on the surface, said observation zone being delimited by a sharp edge, the so-called "observation limit", produced by the mask and the observation edge. The mask obstructs any light susceptible of passing between the illumination edge and the observation edge. Therefore, a weak emergent light passing in front of the observation edge can be easily detected.

It will be understood that the assembly consisting of the mask, the light source and the means of detection of any emergent light can be displaced parallel to the surface against which the mask is disposed. To allow this, the mask is obviously free of any forward projecting object, said objects being susceptible of obstructing such a displacement. This displacement can be performed by any means, including by hand.

It will be understood finally that the characteristics according to d) above make it possible to lengthen the mask to a length D2 without modifying its width E, hence the size of the cells susceptible of being checked. Thus, when the mask+light source+detection means assembly is displaced parallel to the free surface of the honeycomb, a more sizable surface containing proportionally more cells is scanned in the same amount of time, thus increasing the speed of checking. It will also be understood that this characteristic does not exclude the presence of more closely spaced geometrical points A or B. For example, when the illumination edge and the observation edge are two continuous, parallel lines, there exists an infinity of series of points each satisfying this characteristic.

In practice, a light source whose width is at most equal to the width E of the mask is sufficient, said width of the light source being taken from the illumination edge. It will be understood that it is conversely important that the incident light beam to touches the illumination edge so as to be partially cut by the mask, this making it possible to generate a sharp illumination limit by projection on the free surface of the honeycomb. It will also be understood that the detection means need not detect any emergent light very remote from the observation edge. It is sufficient for these detection means to be able to detect any emergent light passing at a distance at most equal to the width E of the mask. It will be understood finally that the adjustment of the actual position of the emergent light thus detectable is dependent on the honeycomb and on the characteristics of the instrument.

Advantageously, M will be at least equal to fifteen, or even fifty, when the regularity of the free surface of the honeycomb so permits. The person skilled in the art will then set the width E to a value slightly greater than the maximum width L1 of the cells having regard to the manufacturing tolerances and to the maximum possible distancing of the mask from the free surface of the honeycomb, this distancing making it possible to absorb the irregularities of said free surface.

The present invention ought not to be confused with the checking instrument disclosed by patent FR-2,716,260 according to the description and Figure four of said patent. Specifically:

1. Figure four shows an illuminating optical fiber 40 and two observing optical fibers 42 disposed on either side of the illuminating fiber 40. What could correspond to the illumination edge and to the observation edge, according to the present invention, consequently comprises just two diametrically opposed geometrical points A on the illuminating optical fiber 40 and two geometrical points B on the observing optical fibers 42 for which the distance E is a minimum, unlike the present invention for which the geometrical points A and B are each at least five in number.

2. The distance D1 between the two geometrical points A is equal to the diameter of the illuminating optical fiber 40 and seems in Figure four to be actually greater than 0.5×E. However, this is fortuitous, since the fatness of this optical fiber does not play any part and is not even mentioned in the description of the cited patent.

3. Since the cells of a honeycomb can only comprise three, four or six sides, it is strictly speaking possible to imagine that the instrument presented by way of state of the art can have an illuminating fiber 40 and up to six observing fibers 42, hence up to six points A and six points B according to the vertices of two regular hexagons. However, only four points out of the six constitute an open line whose two extreme points are at a distance greater than that of any doublet of geometrical points A, whilst according to the present invention, there are at least five thereof.

4. Moreover, this cited patent does not in any way suggest open and thus outspread lines making it possible to scan a wider surface, since if there are six geometrical points A or B, these can only form closed lines, and since this scanning is made impossible by the presence of the pegs 45, said pegs constituting an essential means for centering the optical fibers 40, 42 above the cells. Moreover, this necessity of centering the optical fibers above the cells makes it impossible to use a large number of optical fibers to simultaneously check a large number of cells, on account of the inevitable dimensional manufacturing tolerances for the cells. The present invention, conversely, does not have these limitations. As will also be noted, that which may correspond, in the prior document, to the illumination edge and to the observation edge play no part in this prior document.

In practice, the minimum width E of the mask is at most equal to 36 mm so as to check the honeycombs customarily manufactured in industry. In the case of seal packings in turbomachines, E is less than 3 mm. This minimum width E can drop to values of between 0.6 mm and 1 mm so as to be able to check the honeycombs envisaged in the future.

It will be noted that the illumination edge and the observation edge can be split or continuous, as will be shown by two particular embodiments of the invention, set out later.

Advantageously, the incident light and the emergent light facing said incident light make an angle $\alpha$ of less than 10°, and preferably less than 5°. Such an arrangement makes it possible to reduce the variations in the distance between the incident light and the emergent light when becoming distanced from the mask, this distance being taken parallel to the mask. As a result, the tolerance of the instrument to irregularities of the honeycomb free surface against which this instrument is applied is substantially increased. Specifically, if we consider a segment AB corresponding to a minimum width of the mask, it will be understood that the distance between the projections onto said free surface of the geometrical point A according to the incident light and of the geometrical point B according to the direction of the emergent light varies only very slightly when said free surface is distanced slightly from the mask on account of the manufacturing irregularities which it contains.

The term "emergent light facing said incident light" should be understood to mean that the emergent light is geographically at the same level as the incident light along the mask, in other words that it would be susceptible of originating from said incident light. In practice, the incident light and the emergent light are substantially perpendicular to the mask and converge at the front of said mask.

In a particular embodiment, the mask is flexible in a direction perpendicular to said mask. With such an arrangement, the mask can automatically take the shape of the surface against which it is susceptible of being applied. This arrangement is more particularly intended for surfaces of variable curvature with wide cells, such as the structures of pods or of reversers surrounding turbojet engines.

Advantageously, the instrument comprises an opaque screen, for example a plate, disposed between the light source and the means of detection of the emergent light. Such a screen makes it possible to obstruct any stray light coming from the light source and susceptible of reaching the detection means, thereby facilitating the detection of any emergent light which is much weaker than the incident light.

Advantageously, such a screen extends up to the mask and arrives at this mask from the rear, between the illumination edge and the observation edge, so as to obstruct any stray lights originating from the light source and being susceptible of reaching the observed zone, thereby further facilitating the detection of any emergent light which is much weaker than the incident light.

In a particular embodiment of the instrument which is more particularly reserved for the checking of cells of small width, the mask is integral with the screen and constitutes a lip thereof. It will be understood that the illumination edge and the observation edge are then constituted by the corner which the lip forms with each of the faces of the screen. In practice, in the most frequent case where the cells are perpendicular to the free surface of the honeycomb, the lip is perpendicular to the screen and the screen is positioned above the cells perpendicularly to the free surface.

The invention proposes an instrument of the hand-held scanner type, that is to say an instrument allowing checking by scanning and capable of being held in the hand. Such an instrument is noteworthy in that it comprises:

- a soleplate which is opaque to light and drilled in the thickness direction with a row of at least five illuminated holes and with a row of at least five observed holes parallel to the row of illuminated holes and separated from it by the mask and the screen both integral with said soleplate,
- a light source split into a plurality of elementary light sources, for example LEDs, each of said elementary light sources being disposed at the rear of an illuminated hole and projecting an incident light through said illuminated hole,
- elementary detection means, for example photodiodes or phototransistors, converting the light into electric current, each of said elementary detection means being disposed at the rear of an observed hole and receiving an emergent light passing through said observed hole,
- indicator lights, visible from outside the scanner,
- a plurality of amplifiers each associated with a continuous background separator, each assembly of amplifier+ continuous background separator being connected to P>=1 elementary detector and to an indicator light.

It will be understood that the opaque soleplate makes it possible to rub the hand-held scanner on the free surface of the honeycomb, such a scanner obviously being free of any element projecting forward from the soleplate and susceptible of blocking the displacement of the scanner according to a movement parallel to the free surface of the honeycomb to be checked. It will be understood that the mask is constituted by the part of the surface of the soleplate between the illumination holes and the observation holes, and that the screen is constituted by the volume of the soleplate between said illumination holes and said holes. It will likewise be understood that the soleplate optically isolates the elementary detection means from the ambient light, doing so during the use of the scanner.

Such an instrument also operates with one, two, three or four illumination holes and with one, two, three or four observation holes. However, the inventor agrees to limit the scope of the claim to five holes or more, so as to remain consistent with the general characteristics of the instrument forming the subject of the invention.

Advantageously, the indicator lights are disposed in line and substantially at the rear of the mask, so as to directly signal the locations where the defects are detected.

According to the invention, the fifth object is achieved by an instrument for checking the bonding of the cellular core of a honeycomb to a skin, said instrument being specially designed to implement the present process, said instrument being noteworthy in that it comprises:

a) at least one chamber of photographic type equipped with an objective and with an array of photoelectric receptors, said chamber constituting the means for detecting the emergent light, said objective being situated at the rear of the mask and pointed substantially at the observation edge, the geometrical axis of said objective being substantially orthogonal to said observation edge and forming with the screen an angle of incidence $\beta$ of less than 10°, said objective forming in the chamber a real image of the space in the neighborhood of the observation edge viewed from the rear of the mask, said real image consequently comprising the real image of the observation edge viewed from the rear of the mask, and the off-mask real image of the space in front of the observation edge likewise viewed from the rear of the mask, the array of photoelectric receptors being disposed on the off-mask real image, parallel to the real image of the observation edge and in practice in the neighborhood of said real image of the observation edge, b) a sampling analog/digital converter whose input is connected to the photoelectric receptor array and whose output is connected to a calculator, said converter examining the photoelectric receptors and producing a digital signal of the defects, said digital signal consisting of doublets indicating the signal intensity received by each photoelectric receptor and the position of said photoelectric receptors on the array of photoelectric receptors, c) means for positioning and marching the honeycomb against the mask one in relation to the other, that is to say in a direction of relative travel that is substantially parallel to the mask and preferably, although not necessarily, perpendicular to the illumination and observation edges, d) means for measuring the relative displacement of the honeycomb in front of the mask, said displacement measurement means being likewise connected to the calculator and supplying a digital displacement signal, e) mapping software associated with the calculator, said software constructing a map of the defects on the basis of the digital signal of the defects and of the digital displacement signal.

The term "chamber of photographic type" should be understood to mean a space protected from ambient light making it possible to form an image on a surface with the aid of an optical objective. The actual distance from the array of photoelectric receptors to the real image of the observation edge is adjusted in practice by slightly modifying the orientation of the chamber, this distance having to be equal to d×r, d being the distance between the observation edge and the emergent light to be detected, and r the reduction ratio the observation edge and its real image given by the objective at the back of the chamber.

In practice, the calculator will be a computer and the mapping software will be software customarily used to scan images. It will thus be understood that the map of the defects can be instantaneously displayed on a screen of the computer, printed and/or stored on a magnetic medium automatically or on request. The image thus digitized can also advantageously be reprocessed, for example:

so as to show up the defects in black on a white background, so as to make the map more readable, so as to erase the design of the cells, in order to retain only the representation of the defects and thus to facilitate the visual examination of the map of the defects, so as to automatically identify the good or bad pieces.

The invention will be better understood and the advantages which it affords will become more clearly apparent from the following detailed description of the preferred embodiments and with reference to the accompanying drawings. It will be noted that for the sake of clarity of the drawings, the cells of the honeycomb are in general greatly magnified with respect to the exterior means.

BRIEF DESCRIPTION OF THE DRAWINGS

FIG. 1 illustrates a honeycomb seen in section, as well as the general process for detecting defects.

FIGS. 2 and 3 illustrate the openings of the cells at the surface of the honeycomb, as well as the conditions connecting the illuminated zone and the observed zone as a function of the size of said openings.

FIG. 4 illustrates the simultaneous checking of the defects between two lines of cells, checking by scanning as well as the combination of these two modes of checking.

FIGS. 5 and 6 illustrate the openings of the cells at the surface of the honeycomb, as well as the application of the conditions connecting the illuminated zone and the observed zone as a function of the size of said openings, in the case where the illuminated zone and the observed zone consist of discrete elementary zones.

FIGS. 7 and 8 illustrate the openings of the cells at the surface of the honeycomb, as well as the application of the conditions connecting the illuminated zone and the observed zone as a function of the size of said openings, in the case where the illuminated zone and the observed zone are continuous.

FIG. 9 illustrates a form of implementation of the process by the constructing of an optical image of the defects and by the mapping of said defects with the aid of computerized means of the scanner type. This figure also illustrates the corresponding instrument.

FIG. 10a illustrates the minimum means of a checking instrument in a particular form of implementation according to which the illumination edge and the observation edge are linear and parallel, whilst FIG. 10b illustrates these same means when the illumination edge and the observation edge are split.

FIG. 11 illustrates an instrument of the hand-held scanner type with instantaneous visualization.

FIG. 12 illustrates the electronic means required for the scanner illustrated by FIG. 11.

FIG. 13 illustrates an instrument for checking a frusto-conical honeycomb ferrule.

FIG. 14 illustrates the mounting of the screen on leaf springs as seen from said leaf springs side.

FIG. 15 illustrates the mounting of this same screen seen from the opposite side from said leaf springs.

DESCRIPTION OF THE PREFERRED EMBODIMENTS

Reference will be made firstly to FIG. 1. The honeycomb 1 is at this stage of manufacture a laminated structure comprising a skin 2 onto which is applied a cellular core 3. The cellular core 3 itself comprises a free surface 4 away from the skin 2, as well as a plurality of cells 5 which each open onto the free surface 4 via an opening 6, said cells 5 being mutually adjacent and formed by partitions 7 separating them, said cells 5 also each comprising a bottom 8 formed by the skin 2. The partitions 7 are customarily bonded to the skin 2 by welding, brazing or gluing 9. Locally, this bond 9 may exhibit defects 10 which are manifested by the appearance of a passage 10 passing through a partition 7 and thereby linking two adjacent cells 5 at the bottom 8 of said cells 5. Customarily, and over spans which are limited with respect to the size of the cells, the skin 2 and the free surface 4 are substantially plane and parallel, and the partitions 7 are substantially perpendicular to said skin 2 and to said free surface 4. The cells 5 are substantially identical and of hexagonal shape as illustrated by FIGS. 2, 3 and 5 to 8. In this example, the skin 2 is a flat metallic sheet, the cellular core 3 is likewise metallic and the bond 9 is a brazing.

A light source 15, for example an optical fiber connected to a remote light source (not represented), produces an incident light 16 illuminating the free surface 4 of the honeycomb 1 over a so-called illuminated zone 17 of said free surface 4, said incident light 16 illuminating the interior of the so-called illuminated cells 5a whose openings 6a are at least partially in said illuminated zone 17, said illuminated zone 17 being delimited at least locally by a so-called "illumination" limit 18. Detection means 20 detect any light 21 emerging from the so-called "observed" cells 5b whose openings 6b are at least partially in a so-called "observed" zone 22 at the free surface 4 of the honeycomb 1, said observed zone 22 being delimited at least locally by a so-called "observation" limit 23. The illumination and observation limits 18, 23 overlook one another, and they therefore separate the illuminated and observed zones 17, 22 by a so-called "intermediate" zone 25. If the illuminated zone 17 is above an illuminated cell 5a, if the observed zone 22 is above an observed cell 5b, and if a defect 10 is present in the partition 7 separating the illuminated and observed cells 5a, 5b, a small part of the incident light 16 having penetrated into the illuminated cell 5a passes into the observed cell 5b through the defect 10 and produces a weak emergent light 21 which successively exits the observed cell 5b through its opening 6b, passes through the observed zone 22 and is then detected by the detection means 20.

According to the invention, the minimum distance E between the illumination limit 18 and the observation limit 23 is at least equal to the width L1 of the opening 6 of a cell 5. With such an arrangement, the simultaneous presence of the illuminated zone 17 and of the observed zone 22 above the opening 6 of the same cell 5 is impossible, thus permitting approximate positioning, or even the displacing over the free surface 4 of the honeycomb 1 of the illuminated and observed zones 17, 22, doing so without accidentally causing the emission of an emergent light 21 which would make one believe that a nonexistent defect 10 was present.

For more detail, reference will now be made to FIGS. 1 and 2 simultaneously. The minimum distance E between the illumination limit 18 and the observation limit 23 defines a direction D. This minimum distance E must be at least equal to the width L1 of the opening 6 of a cell taken in the direction D, thereby making it effectively impossible for the illuminated and observed zones 18, 22 to be simultaneously present above the opening 6 of the same cell 5. It will be noted that the geometrical straight line of direction D is normal both to the illumination limit and to the observation limit at the points where it cuts said illumination and observation limits, since this is an extremum.

Since it is impossible for one and the same cell to be present at the same time under the illuminated zone 17 and the observed zone 22, the emergent light 21 can only originate from the incident light fraction 16 which has passed through a defect 10 in a partition 7, said partition 7 being in a favorable position, that is to say between said illuminated zone 17 and said observed zone 22. In the other cases, no emergent light 21 appears. Thus, it is therefore possible to detect bonding defects 10 without any risk of wrongly signaling defects which do not exist and without specific positioning of the illuminated zone 17 and of the observed zone 22. It is sufficient to pass above the defect 10. It will be understood that the process which is the subject of the invention is accordingly very rapid.

Reference will now be made to FIGS. 1 and 3 simultaneously. The width E is advantageously less than the width L2 of the openings 6 of two adjacent cells 5, said width L2 being likewise taken in the direction D. Such an arrangement makes possible the simultaneous presence of the illuminated zone 17 above the opening 6a of an illuminated cell 5a and of the observed zone 22 above the opening 6b of an observed cell 5b, said observed cell 5b being adjacent to the illuminated cell 5a, thus making it possible to improve the resolution of the process down to the size of a cell. Specifically, the process thus makes it possible to detect small brazing defects 10 limited solely to the partition 7 between the adjacent cells 5a and 5b. In the absence of this arrangement, the process would only allow the detection of fatter brazing defects 9 spanning several partitions 7 in the direction D, the light having in this case to pass through several successive defects before exiting into the observed zone 22. Such is the case when the defects extend over an expanse grouping together several cells, for example, due to a lack of binding agent.

Reference will again be made to FIGS. 1 and 2. In this exemplary implementation of the process, a flat opaque screen 29 of thickness E is disposed above the free surface 4. This screen 29 is disposed parallel to the partitions 7, and hence perpendicular to the free surface 4. A lip 26 of the screen 29 is parallel to the free surface 4 and arrives in the neighborhood of said free surface 4. This lip 26 constitutes a mask 26 and is delimited laterally by a first ridge 27, the so-called "illumination edge", which is common with a lateral face 29a of said screen 29. A light source 15 is constituted in this example by a bundle of optical fibers whose ends 15b are disposed against this lateral face 29a and sufficiently rearward of the illumination edge 27, i.e. at least 10 times the diameter of said ends 15b of the optical fibers. The light source 15 produces through its end 15b an incident light beam 16 heading for the free surface 4 and thus produces the illuminated zone 17 on said free surface 4. The incident light beam 16 is delimited by the illumination edge 27 whose projection onto the free surface 4 constitutes the illumination limit 18 of the illuminated zone 17. The further away from the illumination edge 27 the end 15b of the optical fibers is and the closer this illumination edge 27 is to the free surface 4, the sharper the illumination limit 18 will be. It will be understood that the more parallel the incident light beam 16 is to the lateral face 29a in the neighborhood of the illumination edge 27, the further away from the free surface 4 or the closer to it the screen 29 can be without substantially changing the position of the illumination limit 18 on the free surface 4.

The mask 26 is likewise delimited laterally by a second ridge 28, the so-called "observation edge", said observation edge 28 being opposite the illumination edge 27. This observation edge 28 creates the observation limit 23 on the free surface 4. Specifically, the observation edge 28 cooperates with the mask 26 so as to prevent any emergent light 21 from reaching the detection means 20 by passing beyond the observation zone 22 between the illumination edge 18 and the observation edge 23. The mask 26 obstructs any nonreferenced light exiting directly from an illuminated cell 5a heading for the observation means 20. Moreover, the opaque screen 29 protects the observation edge 28, the rear of the mask 26 and the observed zone 22 from the incident light 16 so as not to hinder the detection means 20. Finally, the screen 29 is disposed between the light source 15 and the detection means 20, so as to obstruct any stray light which the light source 15 is susceptible of producing heading for the detection means 20. It will be understood that the size of the screen depends on the design of the light source 15 and of the detection means 20. In this example, the means of detection 20 of the emergent light are here constituted by a magnifying glass 20 allowing visual examination of the defects 10 at the bottom 8 of the cells 5b. In an even simpler form of implementation of the invention reserved for cells of large size, the space 22a above the observed zone 22 is cleared, thus allowing an observer to look directly at the bottom 8 of the cells 5b.

Reference will now be made to FIG. 4. The illumination limit 18 and the observation limit 23, and consequently the intermediate zone 25, extend over a sizable number N of cells 5 and are moved together along a geometrical line of displacement 37 parallel to the free surface 4 of the honeycomb 1. This makes it possible firstly to check N cells at the same time, without having to generate an illumination zone and an observation zone separately above each cell. This makes it possible secondly to check in one single scan along the line of displacement 37 the geometrical surface 38 generated by the joint displacement of the illuminated zone 17 and the observed zone 22 along said line of displacement 37. Small values of N, for example three or more, will be used for example when the free surface of the honeycomb is staircase-like, this sometimes being the case for the honeycombs used as seal packings between stator and rotor of turbomachines. Otherwise, values of N at least equal to fifteen or even fifty have been experimented with successfully when the regularity of the free surface so permits.

Reference will be made to FIGS. 5 and 6 simultaneously. In this example, the illuminated zones 17 are split up into elementary zones, it being possible for each of them to be illuminated for example by an optical fiber, an LED diode or a laser diode. The observed zones 22 are likewise split up into elementary zones, each possibly being observed for example by a photodiode or a phototransistor. The cells 5 being hexagonal, the illuminated and observed elementary zones 17, 22 are in quincunx configuration and extend along a minor diameter of the hexagons with a pitch equal to said minor diameter. The minimum distance E is in this case dependent on the diameters of the illuminated and observed point zones. In practice, E is between one and two times the minor diameter of the hexagonal cells. It will be noted that in the case where the illuminated and observed elementary zones 17, 22 are disposed facing one another, the minimum distance E must be at least equal to a major diameter of the cells.

Reference will now be made to FIGS. 7 and 8 simultaneously. In this example, the illuminated and observed zones 17, 22 are continuous and extend along a minor diameter of the cells. The illumination and observation limits 18, 23 are rectilinear and parallel, and their distance E is at least equal to the major diameter of the hexagonal cells. The light source can consist for example of a bundle of optical fibers or of a tubular halogen bulb, said bulb being placed at a focus of an elliptical cylindrical mirror, the other focus of said mirror arriving in the neighborhood of the illumination limit 18. Through a perspective view, FIG. 8 shows how a defect 10 appears to any observer 20.

In a preferred embodiment of the invention illustrated by FIGS. 9 or 11, the emergent light 21 is converted into electrical signals, thus permitting very rapid reprocessing of the signal by the optoelectronic means.

In a first form of implementation of the process illustrated by FIG. 11, at least one electrical signal actuates an indicator light 75 situated preferably but not necessarily above the emergent light 21 which is at the origin thereof. This makes it possible to signal and pinpoint a defect 10 instantaneously.

In a mode, which is preferred at this level, of implementation of the process illustrated by FIGS. 4 and 9, the illumination and observation limits 18, 23 extend over N consecutive cells 5, N being at least equal to three, said illumination and observation limits 18, 23 being moved along a geometrical line of displacement 37 at the free surface 4 of the honeycomb 1 and thus generating the checked geometrical surface 38:

the position of the electrical signals along the observation limit 23 is marked, the displacement of the illumination and observation limits 18, 23 along the geometrical line of displacement 37 is measured, each electrical signal thus obtained is transferred to a system of coordinates X, Y in the form of a point whose X or Y coordinate is dependent on the position of said electrical signal along the observation limit 23 and whose other coordinate Y or X is dependent on the measurement of the displacement along the geometrical line of displacement 37.

This constitutes a map 45 of the electrical signals detected on the geometrical surface thus checked, said map 45 making it possible to visualize at a single glance all the defects 10 detected on the checked geometrical surface 38. It will be understood that these defects 10 can appear on the map 45 in an isolated manner 46 or in expanses 47.

Advantageously, the illuminated zone 17 and the observed zone 22 are continuous, so as to improve the resolution of the map 45.

Advantageously, a real optical image 50 of the observed zone 22 is constructed with the aid of an objective 51, and the emergent light 21 is detected on the basis of said real optical image 50. The term real image is taken in the sense of geometrical optics and signifies that the image can be gathered on a screen. The effect of such an arrangement is to concentrate and separate the emergent light 21 from any stray lights, and results in a substantial improvement in the tolerance of the process to stray lights and to warping of the honeycomb. It will in fact be understood that the emergent light 21 originates from the defects 10 or from the virtual images of said defects 10 following the reflections on the partitions 7, these defects appearing in the form of small very luminous images inside the real optical image 50 of the observed zone 22. Conversely, an attenuated general fog, or else images of the partitions 7 or of the free surface 4 of the honeycomb 1 will be produced on the real optical image 50 by the stray lights, and will accordingly be very distinct from the images of the defects 10. Thus, detection of the emergent light 21 with a resolution of at least eight points per cell permits good separation and gives suitable images.

In theory, the objective 51 ought to be sufficiently distant from the honeycomb for its center to be overlooking the bottoms 8 of all the cells 5 under the observed zone 22, this theoretical distancing having to be accordingly proportional to the length of the observation limit 23 and to the depth of the cells 5, this theoretical distancing having also to be inversely proportional to the width of said cells 5. In practice, the person skilled in the art will nevertheless be able to reduce this distance within sizable proportions through a few laboratory trials. These trials actually make it possible to note that:

the objective 51 can still capture an emergent light 21 arriving toward its periphery, even if the center of the objective does not itself see the bottom 8 of the cells 5, the reflection on the partitions 7 creates a plurality of virtual images of each defect 10, one or more of said virtual images possibly being captured by the objective 51 through the openings 6 of the cells 5.

In a first form of implementation of the process, the objective 51 is accommodated on the bottoms 8 of the cells 5, so as to produce sharp images of the defects 10.

Advantageously:

the observed zone 22 is itself illuminated by a secondary light source 53, but with a lesser intensity than the illuminated zone 17, the objective 51 is accommodated on a point of accommodation 52 situated between 20% and 50% of the height of the cells 5 from the bottom 8.

Such an arrangement shows up the images of the defects and the image of the cells 5 at the free surface 4 of the honeycomb 1 simultaneously on the map of defects 45, while promoting the sharpness of said defects 10, thus making it possible continuously to check the proper operation of the means used to implement the process. It will in fact be understood that in the absence of defects 10, the map of defects 45 no longer represents anything, and this would also be the case were said means used faulty. Thus, the actual presence of the image of the cells on the map of defects 45 attests to the proper operation of said means used. In practice, the secondary light source 53 is adjusted so that the brightness of the honeycomb 1 thus illuminated is at most equal to that of the images of the defects 10, so as not to cause said defects 10 to disappear in a light fog.

Advantageously, the secondary light source 53 illuminates the observed zone 22 in a direction parallel to the partitions 7. With such an arrangement, the light 54 produced by the secondary light source 53 illuminates the bottom 8 of the observed cells 5b, doing so directly or by reflection on the partitions 7, thereby making it possible to distinguish between a defect 10 through partial melting of the partitions 7 and a defect 10 through lack of brazing. It will in fact be understood that the texture of the bottom 8 of the cells 5 also appears on the map of defects 45. Thus, in the case where this texture reveals the striations of the machining on the skin 2, this signifies that the skin 2 is not covered with brazing and that there is therefore a defect 10 through lack of brazing.

Reference will now be made to FIG. 10a. The checking instrument 60 comprises a mask 26 of width E, said mask 26 being delimited laterally by an illumination edge 27 and an observation edge 28 both continuous, rectilinear and parallel. The width E is quite obviously taken between the illumination edge 27 and the observation edge 28. The illumination edge 27 has a length at least equal to 5×E and consequently comprises at least five successive geometrical points A which are a length D1 greater than or equal to E apart. Likewise, the observation edge 28 has a length at least equal to 5×E and consequently comprises at least five successive geometrical points B which are a length D2 greater than or equal to E apart. A light source 15 is disposed at the rear of said mask 26 and projects an incident light 16 from the rear to the front of the mask 26 and in the neighborhood of the illumination edge 27. Means 20 of detection and of signaling of any emergent light 21 are disposed at the rear of the mask 26, said emergent light 21 passing from the front to the rear of the mask 26 in the neighborhood of the observation edge 28. If an incident light 16 and an emergent light 21 facing one another are considered, the incident light 16 passing in the neighborhood of a geometrical point A of the illumination edge 27, the emergent light 21 passing in the neighborhood of a geometrical point B on the observation edge 28, the segment AB corresponding to a width E of the mask 26, the incident light 16 and the emergent light 21 form an angle α of less than 10°, and preferably less than 5°. It will be noted that the light source 15 can consist for example of a plurality of elementary bulbs or of a tubular bulb associated with a cylindrical reflector disposed parallel to the illumination edge.

Reference will now be made to FIG. 10*b*. In another embodiment of the invention, the mask 26 comprises a first line of circular successive holes through each of which is passed an incident light (not represented) emanating for example from an LED diode. Likewise, this mask 26 comprises a second line of circular successive holes through each of which is detected any emergent light (not represented), detection being performed for example with photodiodes or phototransistors. The holes pass through the mask 26 in the thickness direction, and the two lines of holes are straight and parallel. The set of circumferences of the perforations of the first line constitutes at least in the direction of the second line a discontinuous illumination edge 27. Likewise, the set of circumferences of the second line constitutes at least in the direction of the first line a discontinuous observation edge 28. This mask is more particularly adapted to the scanning of hexagonal cells along a major diameter of said cells and perpendicular to the lines of holes. Therefore, the holes of each line are at a distance D1, D2 equal to a minor diameter of the hexagonal cells, and the ratios D1/E and D2/E are at least equal to 0.5 so that the holes are not too far apart so that an illuminating hole and an observing hole can cover two adjacent cells with a sufficient area. In practice, the person skilled in the art will preferably adopt ratios D1/E and D2/E of between 0.7 and 0.8. It will be noted that in this example, the illumination edge 27 and the observation edge 28 comprise two series of geometrical points complying with the claimed characteristics, i.e. A,A' and B,B' respectively.

In practice, the incident light 16 is not perfect and can also comprise light rays which deviate from the previous characteristics. The person skilled in the art will however take care to ensure that this light source does not tend to cause light rays to pass under the mask.

Reference will now be made to FIGS. 1 and 10*a* simultaneously. It will be understood that the instrument 60 can be laid on the free surface 4 of a honeycomb 1, the opening 6 of whose cells 5 has a width L1 of less than E, whilst the width L2 of the openings 6 of two adjacent cells 5 is greater than E, said width of the openings 6 being taken in the width direction of the mask 26, said instrument making it possible to illuminate a line of cells Sa whose openings 6*a* are under the illuminated zone 17, the incident light 16 passing in front of the illumination edge 27, said instrument 60 likewise making it possible simultaneously to observe the defects 10 through the openings 6*b* situated under the observed zone 22, by virtue of the emergent light 21 emitted, said emergent light 21 passing in front of the observation edge 28. It will be noted that the mask 26 can be curved in the length direction, so as to be able to examine honeycombs 1 substantially forming a portion of a cylinder. In general, when the free surface of the honeycomb can be generated geometrically by displacing a geometrical line referred to as a generator, said mask 26 will be given the shape of said generator. In practice, the mask 26 will be perpendicular to the screen 29 when the cells 5 of the honeycomb 1 are themselves perpendicular to the free surface 4.

In a particular embodiment of the instrument, the mask 26 will be flexible in the length direction. Such an arrangement allows the mask 26 to take the shape of the free surface 4 of the honeycomb 1 against which it is applied. Such an instrument permits the checking of a honeycomb 1 whose free surface 4 is curved and not ruled. The expression ruled surface is understood to mean a surface which can be generated by displacing a straight line or rule. This arrangement is more particularly intended for honeycombs 1 whose cells 5 are of large width, for example on the structures of pods or thrust reversers. The light source 15 can in this case consist of a plurality of elementary sources such as light-emitting diodes disposed immediately to the rear of the illumination edge 27, the support of said light-emitting diodes possibly also being flexible so as to follow the deformations of the flexible mask 26.

Reference will now be made to FIG. 11. In a particular form of the instrument which is more particularly adapted to honeycombs of large area and comprising fat cells, the instrument takes the form of a hand-held scanner 70 susceptible of a displacement 37 by gliding against the free surface 4 of the honeycomb 1. The hand-held scanner 70 comprises a soleplate 72 via which it is applied to the free surface 4. The soleplate 72 is drilled in the thickness direction with an illuminated row of holes 73 and with an observed row of holes 74 substantially parallel to the illuminated row of holes 73 and separated from it by the mask 26 and the screen 29 both integral with the soleplate 73. The hand-held scanner 70 comprises a light source 15 split into a plurality of elementary light sources 15*a*, each of said elementary light sources 15*a* being disposed at the rear of an illuminated hole and projecting an incident light 16 through each illuminated hole 73 so as to illuminate with a sharp outline any object situated in front of the illuminated holes 73 and against the soleplate 72. Each elementary light source 15*a* can consist for example of an LED diode or of a laser diode or of an optical fiber connected to a distant light source (these not being represented). The hand-held scanner 70 also comprises means of detection 20 of the emergent light 21, said means of detection 20 being split into elementary means of detection 20*a*, each of said elementary means of detection 20*a* being disposed at the rear of an observed hole 74 and receiving the emergent light 21 passing through the observed hole 74. Each elementary means of detection 20*a* is an optoelectronic transducer, that is to say converts the light into electrical current, like a photodiode or a phototransistor. It can also be an optical fiber connected to a remote optoelectronic transducer (not represented). Each elementary means of detection 20*a* activates an indicator light 75 by way of an electronic circuit 80. Advantageously, the indicator lights 75 are disposed in line and substantially at the rear of the elementary means of detection 20*a*, so as to directly signal the locations where the defects are detected. It will be understood that the detection and signaling are instantaneous. During the displacement of the hand-held scanner 70 against the free surface 4 of the honeycomb 1, an indicator light 75 comes on whenever the hand-held scanner 70 passes over a defect 10, and it goes off when the hand-held scanner 70 has been displaced.

Reference will now be made to FIG. 12. The electronic circuit 80 comprises at least one generator of energy 81 connected to each light source 15, 15a and powering it via an electric current. The electronic circuit 80 also comprises amplifiers 82 each associated with a continuous background separator 83, each amplifier 82 and continuous background separator 83 assembly being connected to P>=1 contiguous elementary detectors 20a and to an indicator light 75. The amplifier makes it possible to amplify the weak signal emitted by the elementary detectors 20a, and the continuous background separator 83 makes it possible to eliminate the influence of ambient light. This separator can, for example, be of the type set out in patent FR-2,716,260 or U.S. Pat. No. 5,548,400 which were cited with regard to the state of the art. In this case, the energy generator 81 supplies a square-wave electric current, and the continuous background separator 83 is driven from a signal originating from said energy generator 81.

Reference will again be made to FIG. 11. In a particular embodiment of the invention, the scanner 80 comprises a flattened base 85 surmounted by a preferably removable shroud 86. The soleplate 72 is fixed at one end of the base 85, and a skid 87 is fixed at the other end of the base 85, so that the hand-held scanner 70 can be made to glide over the free surface 4 of the honeycomb 1 by pressing on the soleplate 72 and the skid 87. The elementary light sources 15a and the elementary means of detection 20a are disposed in the base 85 overlooking respectively the illuminated holes 73 and the observed holes 74 and to the rear of said holes. The elementary light sources 15a and elementary means of detection 20a are connected to a head printed circuit 88 itself connected to a main printed circuit 89 by a first cable bundle 90 and a first connector 91 disposed on the main printed circuit 89. The main printed circuit 89 is fixed on the base 85 and supports the electronic circuit 80 whose manner of operation has been described previously, this electronic circuit 80 comprising a plurality of channels. The main printed circuit 89 is linked by a second connector 92 and a second cable bundle 93 to a secondary printed circuit 94 on which are connected the indicator lights 75 disposed in line above the shroud 86 by way of a plinth 95.

The electronic circuit 80 of a hand-held scanner 70 of width 100 mm will be able to contain for example 12 channels, thus making it possible to check a surface by scanning over a width of 12 cells of 8 mm. To check a honeycomb 1 whose cells have a different size, it is sufficient to modify the number and the spacing of the optoelectronic elements, as well as the soleplate 72, the plinth 95, the head printed circuit 88, the secondary printed circuit 94, and to connect them to the same main printed circuit 89 and to the same electronic circuit 80 both of which remain unchanged. For example, if the cells are 12 mm wide, it will be possible to check, with this same hand-held scanner 70 of width 100 mm, a surface eight cells wide, four channels of the electronic circuit 80 then remaining unused.

Reference will again be made to FIG. 9. In a preferred embodiment, the instrument 60 comprises a light source 15, a mask 26 and a flat screen 29 of which said mask 26 constitutes a lip perpendicular to said screen 29. The instrument 60 likewise comprises at least one chamber 100 of photographic type, said chamber being equipped with an objective 51 and with an array of photoelectric receptors 101. This objective 51 with geometrical axis 51a is situated at the rear of the mask 26 and is pointed substantially at the observation edge 28 of the mask 26, the geometrical axis 51a being substantially orthogonal to this observation edge 28 and forming with the screen 29 an angle of incidence β of less than 10°. The objective 51 forms in the chamber 100 a real image 50 of the space in the neighborhood of the observation edge 28 viewed from the rear of the mask 26. This real image 50 consequently consists of three parts, i.e. in succession: the real image 102 of the mask 26 viewed from the rear, if this mask 26 is not hidden by the screen 29, the real image 103 of the observation edge 28 likewise viewed from the rear of the mask 26, and the off-mask real image 104 of the space in front of the observation edge 28 likewise viewed from the rear of the mask 26. The array of photoelectric receptors 101 receives the light coming from the objective 51 and is disposed on the off-mask real image 104, parallel to the real image of the observation edge 103 and in the neighborhood of said real image of the observation edge 103. The array of photoelectric receptors 101 need not be on the geometrical axis 51a of the objective 50, it is sufficient for it not to be too remote therefrom in order for it to be able to gather a correct image. The person skilled in the art will set the position of the chamber 100 in such a way that the defects 10 are shown up as well as possible on the map 45.

The array of photoelectric receptors 101 is connected to the input of an analog/digital converter 112 whose output is itself connected to a calculator 113. This converter 112 examines the photoelectric receptors 101 and produces a digital signal 114 of the defects which consist of doublets indicating the intensity of the signals received by each photoelectric receptor and the position of said photoelectric receptor in the array of photoelectric receptors 101.

The instrument 60 likewise comprises means 116 for positioning and marching the honeycomb 1 against the mask 26 and relative to it in a direction of marching 37 substantially parallel to the mask 26 and preferably, but not necessarily, perpendicular to the illumination and observation edges 27, 28. The honeycomb 1 can be movable and the mask 26 fixed, for example in the case of a fixed installation, or vice versa, for example in the case of an instrument of the hand-held scanner type.

In practice, the means 116 for positioning and marching the honeycomb 1 against the mask 26 maintains the distance between the free surface 4 and the mask 26 a distance of less than or equal to the width E of the mask. In the contrary case, the risk of the appearance of false flaw signals resulting from the irregularities of said free surface 4 becomes considerable.

The instrument 60 likewise comprises means 117 for measuring the displacement 37 of the honeycomb 1 in front of the mask 26, said displacement measurement means 117 being likewise connected to the calculator 114 and supplying a digital displacement signal 118. Finally, the instrument 60 comprises mapping software associated with the calculator 113, said software constructing a map of defects 45 on the basis of the digital signal of the defects 114 and of the digital displacement signal 118.

The operator will, via a few experiments, adjust the orientation of the chamber 100, and thereby the relative position of the real image 103 of the observation edge 28 in such a way that the defects 10 are shown up as well as possible on the map 45.

The calculator 113 can be a microcomputer available on the market, and the mapping software can be one of those items of software which are commonly marketed together with scanners required to be used with such a microcomputer. This solution is economical and makes it possible to display the map 45 of defects on the screen 120 directly and in real time, it also being possible for this map 45 to be output on request to a printer 121 connected to the microcomputer.

Advantageously, the light source 15 is a bundle of optical fibers connected to a remote light source, said optical fibers being situated at the rear of the mask 26 overlooking the illumination edge 27, the end 15*b* of said optical fibers being set back from the illumination edge 27, for example by 20 times the diameter of said optical fibers, said bundle of optical fibers being oriented perpendicularly to the mask 26 and parallel to the illumination edge 27. In the case where the mask 26 consists simply of a lip of the screen 29, these optical fibers will simply be applied against the illuminated face 29*a* of the screen 29, that is to say on the light source 15 side. This arrangement has the advantage of being relatively unbulky, and it makes it possible to produce a very intense incident light 16 perfectly oriented with respect to the cells of the honeycomb. Specifically, this incident light 16 arrives in front of the illumination edge 27, forming a sheet of light which is very perpendicular to the mask 26. The tolerance to the irregularities of the free surface 4 of the honeycomb 1 becomes considerable. It has been possible to distance the mask 26 from said free surface 4 up to a distance equal to twice the width E of the mask. It may be noted that such a result could theoretically be obtained also by using an incident light produced and rendered parallel by a point light source and an optical condenser. Such a solution would however be tricky to implement owing to the bulkiness of the light source+optical condenser assembly, contrary to the solution implementing a bundle of optical fibers.

The instrument 60 may comprise just a single objective 51 and a single chamber 100. This solution is the simplest in the case of a fixed installation permitting a sufficient distance between the objective 51 and the mask 26 to simultaneously observe a line of cells over a sufficient length. The instrument 60 can also comprise N>1 objectives 51 associated with N>1 chambers 100 disposed in parallel. Such an arrangement has the effect of dividing by N the distance between the observation edge 28 and the real images 50, and as a result substantially reduces the bulkiness of the instrument 60. The latter solution is more particularly adapted to instruments 60 which are required to exhibit low bulkiness, for example of the hand-held scanner type. It also makes it possible to use low-price objectives of small size, for example commonly-marketed objectives employing aspherical molded lenses, whilst preserving very good resolution of the real image 50 produced. In either case, the objectives 51 may be brought close to the observation edge 28 and the chambers 100 may be shortened by breaking the light beams with mirrors.

The instrument also comprises a secondary light source 53 secured to the instrument 60, said secondary light source 53 being however weaker than the light source 15, said secondary light source 53 being disposed on the same side of the screen 29 as the detection means 20, said secondary light source 53 producing a secondary light 54 going from the rear of the mask 26 to the front of said mask 26, said secondary light 54 passing in front of the observation edge 28 and arriving at least flush with the observation edge 28. It will be understood that such a secondary light 54 is susceptible of illuminating any object situated in front of the mask 26, protruding from the mask 26 on the observation edge 28 side and situated in the neighborhood of said mask 26, such as the free surface 4 of the honeycomb 1. By arriving at least flush with the observation edge 28, the part of the free surface 4 whose image will be captured by the chamber 100 is illuminated. In practice, the secondary light 54 is at least ten times weaker than the incident light 16.

Advantageously, the secondary light 54 is parallel to the screen 29 and orthogonal to the observation edge 28. This makes it possible to illuminate the bottom 8 of the observed cells 5*b*.

In practice, the relative displacement 37 between the positioning and marching means 116 and the mask 26 is ensured by a motor 130 acting by way of a geared down transmission 131. Advantageously, the means of measuring the relative displacement 117 will be disposed between said motor 130 and said geared down transmission 131. It will be understood that with such an arrangement, the measurement of the relative displacement is performed on a mechanical member displacing rapidly over a large length, thus making it possible to reduce the minimum displacement susceptible of measurement, and thereby to improve the fineness of the details susceptible of appearing on the map 45.

Reference will now be made to FIG. 13. Honeycomb 1 ferrules 135 are frequently found on turbomachines, especially for aircraft, said ferrules 135 being circular and cylindrical, or usually frustoconical shaped, the openings of the cells being directed inward, said ferrules 135 being used as seal packings between the blades of the rotor and the stator of the turbomachine. When the ferrule 135 is monobloc at this stage of manufacture, the only known method of checking consists in illuminating a cell and in detecting the light passing through the brazing defects into the adjacent cells. This may be done with the aid of an endoscope or with the aid of the instrument disclosed by patent FR-2,716,260 cited in regard to the state of the art. In both cases, this check is very slow and can only be done by sampling. The present invention makes it possible to perform such a check rapidly and exhaustively, that is to say for the entire free surface of the honeycomb. To do this, the positioning and marching means 116 comprise a turntable 136 for marching the honeycomb ferrule 135 past the mask 26, and a circular cradle 137 for positioning said honeycomb ferrule 135 in front of the mask 26, said circular cradle 137 being disposed on the turntable 136 and centered with respect to the geometrical axis 136*a* of rotation of said turntable 136. This turntable 136 being driven by the motor 130 by way of the geared down transmission 131, the means of measuring the relative displacement 117 being disposed between the motor 130 and the geared down transmission 131.

In the case where the conicity of the ferrule 135 is too small or zero, the geometrical axis 51*a* of the objective 51 then interfering with said ferrule 135, the objective 51 is disposed above the ferrule 135 and will look at the inside surface of said ferrule 135 by way of a mirror (not represented).

With such an instrument, it has been possible to check ferrules 135 with a staircased profile whose steps are of the order of 10 mm, by giving the mask 26 in its thickness direction a profile complementary to that of the profile of the ferrule.

In the case where at this stage of manufacture the ferrule 135 takes the form of unreferenced independent sectors, these sectors will advantageously be disposed side-by-side in the cradle 137 so as to be checked together.

Reference will again be made to FIG. 9. Advantageously, the mask 26 and the positioning and marching means 116 are slideable one with respect to the other in a direction perpendicular to the illumination edge 27 and to the observation edge 28, said direction being parallel to the screen 29, the instrument 60 also comprising elastic return means which automatically bring together said mask 26 and said positioning and marching means 116. With such an arrangement, the mask 26 arrives automatically against any object disposed in front of it and in the neighborhood of it, in particular the free surface 4 of the honeycomb 1, thus making it possible to check honeycombs 1 whose free surface 4 is more irregular. Specifically, this avoids too considerable a spacing between the mask 26 and the free surface 4, such as would otherwise produce false flaw signals. In a particular embodiment, the mask 26 is applied continuously against the honeycomb 1 while said honeycomb 1 marches past in front of said mask 26, thus maintaining at a minimum the space susceptible of appearing between the mask 26 and the honeycomb 1 and thereby making it possible to increase the tolerance of the instrument to irregularities of shape of the honeycomb 1. In another embodiment of the invention, the mask 26 is held, for example by an abutment. By adjusting this abutment to a limited distance from the free surface 4, contact and continual rubbing of said mask 26 on said free surface 4 are avoided, this rubbing producing the wearing of the mask and periodically necessitating its replacement. However, in the case where the free surface 4 is too irregular, the latter would arrive against the mask 26 and would push it rearward without damage.

Reference will now be made to FIG. 14, and the term mask/screen 138 will designate the assembly consisting of the mask 26 and the screen 29. The mask/screen assembly 138 is held at the front, that is to say near the mask 26, by two flat front leaf springs 140 disposed substantially parallel to the mask 26, and hence perpendicular to the screen 29. The mask/screen assembly 138 is also held at the rear by at least one rear leaf spring 141, said rear springs 141 being disposed substantially parallel to the front springs 140, said rear springs 141 being twisted so as to make at least a quarter of a revolution. Such an arrangement makes it possible to hold the mask/screen assembly 138 without play and without rubbing, with two degrees of freedom, i.e. a translational freedom 142 in a direction substantially perpendicular to the mask 26, and a rotational freedom 143 according to a geometrical axis of rotation 143a substantially parallel to the front springs 140 and situated substantially midway between said front springs 140. It will be understood that the rotational freedom is obtained by twisting the rear springs 141. When the mask/screen assembly 138 is pressed against the free surface 4 of the honeycomb 1, it can then remain hard up against said free surface 4 during the relative marching 37 of the honeycomb 1 past the mask 26, this being despite the irregularities or warping of said free surface 4.

This arrangement has several advantages:
  the mask/screen assembly 138 is maintained without play and without rubbing, hence without wear;
  during the displacements of the mask/screen assembly 138 in accordance with the two degrees of freedom 142 and 143, the lateral displacement of the real image 50 remains of second order and hence very small, and thus does not hamper the adjustment of the detection means with respect to the mask 26;
  the movable pieces can be very lightweight, thus making it possible to march the honeycomb 1 more rapidly past the mask 26.

Reference will now be made to FIGS. 14 and 15 simultaneously. Advantageously, the screen 29 is a thin plate made of lightweight alloy or a reinforcing fiber+polymerized resin composite material. The mask 26 is constituted by a lip of a wear piece or mask holder 144 bonded in an irremovable manner to the screen 29, said mask holder 144 possibly itself being a plate made of hard metal comprising a rectilinear and perpendicular lip constituting the mask 26, said plate receiving a treatment at least at the level of the mask 26 so as to improve its rubbing qualities and its wear resistance, this treatment possibly being for example a nitriding. The rear springs 141 will be two in number and will be disposed together with the front springs 140 approximately according to the corners of a square. At their ends, the front and rear springs 140, 141 comprise perpendicular claws 140a, 140b and 141a, 141b respectively, said springs 140, 141 being tied to the mask/screen assembly by the claws 140a, 141a, said springs 140, 141 being tied to a support (not represented) by the other claws 140b, 141b. The light source 15 is a bundle of optical fibers applied against a face of the screen 29 and passing between the springs 140, 141. The screen 26 and the mask holder 144 will receive a matt black surface treatment.

What is claimed is:

1. A process for checking the bonding of the cellular core of a honeycomb to a skin, said honeycomb comprising a cellular core including adjacent cells delimited laterally by partitions, said core being bonded at one side of said skin whilst at this stage of manufacture the other side constitutes a free surface where mouths of said cells are open, said process comprising the following steps:
  using a light source to illuminate an illuminated zone on said free surface of said honeycomb; and
  detecting emergent light exiting the cells in an observed zone likewise on said free surface;
  wherein a minimum distance between said illuminated zone and said observed zone being denoted E and defining a direction D, and said distance E being at least equal to a maximum width L1 of said mouths, said width L1 being taken in the direction D.

2. The process as claimed in claim 1, wherein said distance E is less than the width L2 of the mouths of two adjacent cells, said width L2 being likewise taken in the direction D.

3. The process as claimed in claim 1, wherein the limits of the illuminated and observed zones facing one another are referred to respectively as the illumination limit and the observation limit, and the zone between said illumination limit and said observation limit is referred to as the intermediate zone, and wherein said process includes the step of covering said intermediate zone by a mask which is opaque to light, said mask being bordered laterally by an illumination edge and an observation edge opposite to one another, said illumination edge having the same shape as the illumination limit and being positioned above it, said observation edge having the same shape as the observation limit and being positioned above it, and the incident light touching said illumination edge.

4. The process as claimed in claim 3, wherein the incident light supplied by said light source is substantially perpendicular to said free surface of the honeycomb.

5. The process as claimed in claim 4, wherein said illumination and observation limits extend over N consecutive cells, where N is at least equal to three.

6. The process as claimed in claim 4, wherein said illumination and observation limits are moved together along a geometrical line of displacement at the free surface of said honeycomb.

7. The process as claimed in claim 4, wherein said illumination and observation limits extend over N consecutive cells, where N is at least equal to three, and wherein said illumination and observation limits are moved together along a geometrical line of displacement at the free surface of said honeycomb.

8. The process as claimed in claim 7, wherein:
  a joint displacement of said illumination limit and of said observation limit along said geometrical line of displacement is measured;

the positions of the emergent light appearing along said observation limit are marked; and the appearances of the emergent light are indicated on a system of coordinates X,Y, the measurement of the displacement being plotted on one of the coordinates X,Y and the corresponding positions of the emergent light being plotted on the other coordinate Y,X.

9. The process as claimed in claim 8, wherein said observed zone is continuous, wherein a real optical image of said observed zone is constructed with the aid of an objective, and wherein the emergent light is detected on the basis of said real optical image.

10. The process as claimed in claim 9, wherein said objective is accommodated at the bottom of said cells.

11. The process as claimed in claim 9, wherein:

said observed zone is itself illuminated by a secondary light source, but with a lesser intensity than said illuminated zone; and said objective is accommodated at a point situated between 20% and 50% of the height of said cells from the bottom.

12. The process as claimed in claim 11, wherein said secondary light source illuminates the observed zone in a direction parallel to said partitions.

13. The process as claimed in claim 1, wherein the space above said observed zone is clear, and wherein the detection of said emergent light is visual.

14. An instrument for checking the bonding of the cellular core of a honeycomb to a skin, said instrument comprising:

a) an opaque mask delimited laterally by an illumination edge and an observation edge opposite said illumination edge;

b) a light source disposed to a rear of the mask, said light source being secured to the mask and producing an incident light beam going from the rear of the mask to in front of the mask, said incident light beam being partially cut by the mask and the illumination edge, said mask thus extending partially outside the incident light beam on the observation edge side, said observation edge itself being outside said incident light beam; and c) detection means for detecting emergent light going from the front to the rear of the mask, said detection means being secured to the mask, said emergent light passing in front of the observation edge in the neighborhood thereof;

wherein at M successive geometrical points A on the illumination edge and at M successive geometrical points B on the observation edge, M being at least equal to five, the distance AB between the illumination edge and the observation edge is a minimum and equal to E, a distance D1 between two geometrical points A being at least equal to 0.5×E, a distance D2 between two geometrical points B also being at least equal to 0.5×E, the M geometrical points A forming an open line whose two geometrical points A situated at its ends are a distance apart greater than that of any other doublet of geometrical points A, and the M geometrical points B likewise forming an open line whose two geometrical points B at its ends are a distance apart greater than that of any other doublet of geometrical points B.

15. The instrument as claimed in claim 14, wherein the minimum width E of said mask is at most equal to 36 mm.

16. The instrument as claimed in claim 14, wherein the incident light and the emergent light facing said incident light make an angle α of less than 10°.

17. The instrument as claimed in claim 16, wherein said mask is flexible in a direction perpendicular to said mask.

18. The instrument as claimed in claim 14, including an opaque screen disposed between said light source and the emergent light detection means so as to prevent any stray light from the light source reaching the detection means.

19. The instrument as claimed in claim 18, wherein said screen extends up to the mask from the rear, and is joined to the mask between the illumination edge and the observation edge so as to prevent any stray light from the light source reaching the observed zone.

20. The instrument as claimed in claim 19, wherein said mask is integral with said screen and constitutes a lip thereof.

21. The instrument as claimed in claim 18, including a soleplate which is opaque to light and which has holes drilled through it in the thickness direction to form a row of at least five illuminated holes and a row of a least five observed holes parallel to the row of illuminated holes and separated therefrom by said mask and said screen, both of which are integral with said soleplate, and wherein:

said light source comprises a plurality of elementary light sources, each of said elementary light sources being disposed at the rear of an illuminated hole and projecting incident light through said illuminated holes;

and said detection means comprises a plurality of elementary detectors for converting light into electric current, each of said elementary detectors being disposed at the rear of an observed hole and receiving emergent light passing through said observed hole, indicator lights, and a plurality of amplifiers each associated with a continuous background separator, each assembly of amplifier and continuous background separator being connected to P>=1 elementary detectors and to an indicator light.

22. The instrument as claimed in claim 21, wherein said indicator lights are disposed in line and substantially at the rear of said mask.

23. The instrument as claimed in claim 18, including:

a) at least one chamber of photographic type, said chamber being equipped with an objective and with an array of photoelectric receptors, said chamber equipped with said objective and said photoelectric receptors constituting said detection means for detecting said emergent light, said objective being situated to the rear of said mask and pointed substantially at the observation edge, the geometrical axis of said objective being substantially orthogonal to said observation edge and forming with said screen an angle of incidence β of less than 10°, said objective forming in said chamber a real image of the space in the neighborhood of the observation edge viewed from the rear of the mask, said real image comprising the real image of the observation edge viewed from the rear of the mask and the off-mask real image of the space in front of the observation edge also viewed from the rear of the mask, said array of photoelectric receptors being disposed on the off-mask real image parallel to the real image of the observation edge;

b) a sampling analog/digital converter whose input is connected to said photoelectric receptors and whose output is connected to a calculator, said converter examining said photoelectric receptors and producing a digital signal of the defects which consists of doublets indicating the signal intensity received by each photoelectric receptor and the position of said photoelectric receptor in the array of photoelectric receptors;

c) means for positioning and moving the honeycomb against and past the mask, one relative to the other;

d) means for measuring the relative displacement of the honeycomb in front of the mask, said displacement measuring means being connected to said calculator and supplying a digital displacement signal; and e) mapping software associated with said calculator, said software constructing a map of the defects on the basis of the digital signal of the defects and of the digital displacement signal.

24. The instrument as claimed in claim 23, wherein said light source comprises a bundle of optical fibers connected to a more remote light source, said optical fibers being situated to the rear of the mask overlooking said illumination edge, the ends of said optical fibers being set back from the illumination edge, and said bundle of optical fibers being oriented perpendicularly to the mask and parallel to the illumination edge.

25. The instrument as claimed in claim 23, further comprising N>1 objectives associated with N>1 chambers disposed in parallel.

26. The instrument as claimed in claim 23, including a secondary light source which is weaker than the main light source, said secondary light source being disposed on the same side of the screen as said chamber and producing secondary light passing from the rear of the mask to the front of said mask, said secondary light passing in front of the observation edge and arriving at least flush with the observation edge.

27. The instrument as claimed in claim 26, wherein said secondary light is parallel to the screen and orthogonal to the observation edge.

28. The instrument as claimed in claim 23, wherein the relative displacement between the positioning and moving means and said mask is ensured by a motor acting by way of a geared down transmission, and wherein the means for measuring the relative displacement is disposed between said motor and said geared down transmission.

29. The instrument as claimed in claim 23, wherein the positioning and moving means comprise a turntable and a circular cradle, said circular cradle being disposed on the turntable and centered with respect to the geometrical axis of rotation of said turntable.

30. The instrument as claimed in claim 23, wherein the said mask and the positioning and moving means are slidable one with respect to the other in a plane perpendicular to the mask and parallel to the illumination and observation edges, the instrument comprising elastic return means which automatically bring together said mask and said positioning and moving means.

31. The instrument as claimed in claim 30, wherein the mask and screen assembly is held at the front, that is to say near the mask, by two flat front leaf springs disposed parallel to the mask and perpendicular to the screen, and is also held at the rear by at least one rear leaf spring disposed parallel to the front leaf springs, said rear springs being twisted so as to make at least a quarter of a revolution.

* * * * *